(12) United States Patent
Sheets et al.

(10) Patent No.: US 8,853,422 B2
(45) Date of Patent: Oct. 7, 2014

(54) PYRROLIDINE-2,5-DIONE DERIVATIVES FOR USE IN FRICTION MODIFICATION

(71) Applicant: Afton Chemical Corporation, Richmond, VA (US)

(72) Inventors: Roger M. Sheets, Pagosa Springs, CO (US); Nubar Ozbalik, Midlothian, VA (US)

(73) Assignee: Afton Chemical Corporation, Richmond, VA (US)

( * ) Notice: Subject to any disclaimer, the term of this patent is extended or adjusted under 35 U.S.C. 154(b) by 0 days.

(21) Appl. No.: 14/020,082

(22) Filed: Sep. 6, 2013

(65) Prior Publication Data

US 2014/0011721 A1    Jan. 9, 2014

Related U.S. Application Data

(62) Division of application No. 12/665,459, filed as application No. PCT/US2008/067074 on Jun. 16, 2008, now Pat. No. 8,624,038.

(60) Provisional application No. 60/944,872, filed on Jun. 19, 2007.

(51) Int. Cl.
| | |
|---|---|
| *C07D 207/40* | (2006.01) |
| *C10M 133/56* | (2006.01) |
| *C07D 207/412* | (2006.01) |
| *C10M 149/06* | (2006.01) |
| *C10M 133/44* | (2006.01) |
| *C10M 133/16* | (2006.01) |

(52) U.S. Cl.
CPC ........... *C10M 133/44* (2013.01); *C10M 133/56* (2013.01); *C10M 2215/086* (2013.01); *C07D 207/412* (2013.01); *C10N 2240/04* (2013.01); *C10M 2201/18* (2013.01); *C10N 2240/045* (2013.01); *C10M 2219/044* (2013.01); *C10M 2215/28* (2013.01); *C10N 2240/106* (2013.01); *C10N 2240/044* (2013.01); *C10M 2215/04* (2013.01); *C10M 2215/02* (2013.01); *C10M 149/06* (2013.01); *C10M 2203/024* (2013.01); *C10N 2230/02* (2013.01); *C10N 2230/76* (2013.01); *C10M 2207/34* (2013.01); *C10N 2230/45* (2013.01); *C10M 2207/282* (2013.01); *C10N 2230/06* (2013.01); *C10N 2240/12* (2013.01); *C10N 2240/105* (2013.01); *C10N 2220/022* (2013.01); *C10N 2260/12* (2013.01); *C10N 2230/04* (2013.01); *C10M 2207/122* (2013.01); *C10M 133/16* (2013.01); *C10N 2240/042* (2013.01); *C10M 2215/08* (2013.01); *C10M 2217/043* (2013.01); *C10N 2260/14* (2013.01); *C10M 2207/129* (2013.01); *C10N 2240/10* (2013.01); *C10M 2217/024* (2013.01); *C10M 2223/12* (2013.01); *C10M 2219/042* (2013.01)

USPC ........... 548/545; 548/520; 508/192; 508/287; 508/293

(58) Field of Classification Search
USPC ........... 508/192, 287, 293, 294; 548/520, 545
See application file for complete search history.

(56) References Cited

U.S. PATENT DOCUMENTS

| | | | |
|---|---|---|---|
| 4,105,571 | A | 8/1978 | Shaub et al. |
| 5,087,788 | A | 2/1992 | Wu |
| 5,942,470 | A | 8/1999 | Norman et al. |
| 2003/0139303 | A1 | 7/2003 | Scharf et al. |
| 2005/0065043 | A1 | 3/2005 | Henly |
| 2006/0217273 | A1* | 9/2006 | Ozbalik et al. ................. 508/269 |
| 2007/0191239 | A1 | 8/2007 | Matsuoka et al. |
| 2008/0153972 | A1 | 6/2008 | Wang et al. |

FOREIGN PATENT DOCUMENTS

| | | |
|---|---|---|
| EP | 0020037 | 12/1980 |
| EP | 0856042 | 8/1998 |
| EP | 1151994 | 11/2001 |
| EP | 1424322 | 6/2004 |
| WO | 9714772 | 4/1997 |
| WO | 2005037281 | 4/2005 |
| WO | 2006043709 | 4/2006 |

OTHER PUBLICATIONS

Arnaud Pierre Schaffner et al: Radical-Mediated Three-Component Coupling of Alkenes; Helvetica Chimica Acta, Verlag Helvetica Chimica Acta. Basel, CH, vol. 89, Jan. 1, 2006, pp. 2450-2461.

* cited by examiner

*Primary Examiner* — Vishal Vasisth
(74) *Attorney, Agent, or Firm* — Luedeka Neely Group, P.C.

(57) ABSTRACT

The present disclosure relates to a compound of the formula I or a tribologically acceptable salt, solvate, hydrate, or proadditive thereof, wherein R1, R2 and R4 are as defined herein. Such novel pyrrolidine, or succinimide, derivatives may be useful as friction modifiers in lubricant compositions. This disclosure also relates to a method of using such friction modifier compounds in lubricating fluid formulations to lubricate machine parts, including gear, axle, engine, and transmission parts, and to lubricant compositions containing such friction modifier compounds.

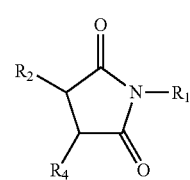

I

4 Claims, No Drawings

PYRROLIDINE-2,5-DIONE DERIVATIVES FOR USE IN FRICTION MODIFICATION

This application is a DIV of Ser. No. 12/665,459 filed Feb. 5, 2010, which is a 371 of PCT/US08/67074, filed Jun. 16, 2008, which claims benefit of 60/944,872, filed Jun. 19, 2007.

TECHNICAL FIELD

This disclosure relates to lubricant additives that may be used in a lubricating fluid having satisfactory friction characteristics without sacrificing low temperature viscometric performance. The disclosure also relates to the preparation of such lubricant additives and concentrates containing such lubricant additives, as well as devices lubricated with a lubricating fluid that includes such lubricant additives.

BACKGROUND

Friction modifier compounds used in lubricant formulations may generally have a formula comprising a polar functional group attached to a hydrophobic hydrocarbon chain that preferably has a suitable formula and a suitable number of carbon atoms in order to exhibit oil solubility. Molecules of this nature may typically be used in amounts ranging from about 0.01 to about 0.5 wt. %, based on the weight of the fully formulated lubricant, and may be capable of providing a suitable degree of fresh oil shudder protection in automatic transmission fluids (ATFs) or other lubricating fluids; however, they may fail in durability testing due to a limited quantity present in the oil. One approach to circumvent this problem is to use friction modifiers at levels ranging as high as from about 3 to about 5 wt. %. However, an important limitation to this practice may involve the low temperature viscometrics property, which is measured as Brookfield Viscosity at −40° C. (BV −40). Finished lubricants having a high level of conventional friction modifiers may suffer from unacceptably high BV −40 values.

Typifying the aforementioned friction modifier compounds are additives for lubricants as described in EP 0020037A1 that may be characterized as oil-soluble aliphatic hydrocarbyl-substituted succinimide or succinamide materials wherein the hydrocarbyl group that is bonded to the succinimide group contains 12 to 36 carbon atoms and is preferably derived from a linear α-olefin, and more preferably derived from an isomerized linear α-olefin, in order to improve oil solubility.

A friction modifier according to EP 0020037A1, with the hydrocarbyl group based on an isomerized linear α-olefin, suffers from poor low temperature viscometrics, when measured as Brookfield Viscosity at −40° C. (BV −40). For instance, a formulation representative of a preferred lubricant additive in EP 0020037A1 may be formulated as a friction modifier in a power transmitting fluid formulation that may have adequate durability performance. However, a formulation containing such a friction modifier at higher concentrations, such as 3.5% by weight, suffers from grossly inadequate low temperature viscometrics. At low temperature the viscosity of such a formulation may be as high as about 30,000 cP, which is a commercially undesirable viscosity with respect to automatic transmission lubricants.

In principle, the poor low temperature viscometrics might be compensated for by adding an expensive synthetic ester to the lubricant. However, the amount of synthetic ester required in order to lower the BV −40 to the desired level of roughly 10,000 cP or less is simply not economically attractive due to the increase in overall production costs.

Yet another drawback to the conventional friction modifier formulation relates to its aesthetic features apparent in the form of slight haze or sediment at higher treat rates, such as about 3.5 wt. %. Due to its dark brown color, finished oils with this formulation at high treat rates are darker in color. A still further drawback is that this formulation is solid at room temperature and requires additional heating for transfer and blending.

There is no apparent disclosure or recognition in EP 0020037A1 suggesting an awareness of the low temperature performance problem with its preferred friction modifiers, nor is there any suggestion of a commercially viable solution to the low temperature viscometrics problem.

Accordingly, there is a need for an economically attractive friction modifier that may be used at higher concentration levels, such as greater than 2% by weight of the fully formulated fluid, in a lubricating fluid or power transmitting fluid, such as an automatic transmission fluid (ATF), to provide improved friction durability. Such a friction modifier may also provide an aesthetically acceptable product that does not suffer from the poor low temperature properties that are observed with conventional formulations incorporating preferred friction modifiers according to EP 0020037A1.

It has now been discovered that certain novel compounds as described hereinbelow may be readily formulated into lubricating compositions to afford a unique solution for providing desired characteristics, such as improved friction durability and low temperature viscometric properties.

SUMMARY

The present disclosure describes a novel lubricant additive that may be capable of being used at relatively high treatment rates, and that may meet the friction durability requirements of Original Equipment Manufacturers (OEMs) worldwide as well as service fill applications. The presently disclosed lubricant additive may provide excellent low temperature viscosity. For example, the lubricant composition as described herein may have a BV −40 of less than about 10,000 cP based on the lubricant composition. As a further example, the lubricant composition may have a BV −40 of as low as about 8,000 cP, or as a further example as low as about 6,000 cP.

The present disclosure further provides that such a novel lubricant additive may be a liquid at room temperature and provide handling benefits over certain other known, preferred concurrent formulations.

An embodiment of the present disclosure describes a novel lubricant additive of the succinimide class, such succinimide having a thermodynamically stable, tri-substituted internal olefin having about 12 to about 36 carbon atoms and a vinyl substituted alkyl group, typically a methyl group. In contrast to a representative preferred lubricant additive of EP 0020037A1, the presently disclosed lubricant additive may be included in formulations for lubricating fluids that exhibit satisfactory low temperature viscometrics. Such a formulation may both avoid the need for high amounts of synthetic esters and have better aesthetics in comparison to the case of using an isomerized linear α-olefin.

An embodiment comprises a compound as represented by formula I below:

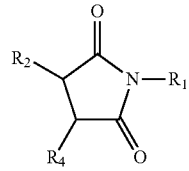

or a tribologically acceptable salt, solvate, hydrate, or proadditive thereof, wherein $R_1$ is selected from the group consisting of: hydrogen, $-(C_1-C_6)$alkyl, $-(C_1-C_6)$alkenyl, $-(C_3-C_7)$cycloalkyl, $-(C_2-C_9)$heterocyclyl, and a radical having formula II below, where z may be from 1-10;

wherein said $-(C_1-C_6)$alkyl, $-(C_1-C_6)$alkenyl, $-(C_3-C_7)$ cycloalkyl, and $-(C_2-C_9)$heterocyclyl substituents are optionally substituted by one to three moieties independently selected from the group consisting of hydrogen, halogen, hydroxyl, $-(C_1-C_{16})$alkyl, $-(C_1-C_{16})$alkenyl, $-CN$, $-NR_8R_9$, $-OR_8$, $-(C_3-C_7)$cycloalkyl, $-(C_2-C_9)$heterocyclyl, $-CO_2R_{15}$, $-SO_2NR_8R_9$, $NR_{15}SO_2R_{10}$, $-SO_2R_{10}$ and $-CONR_8R_{11}$; wherein $R_8$ and $R_{11}$ of said $-CONR_8R_{11}$ group may be taken together with the atoms to which they are attached to form a $-(C_2-C_9)$heterocyclyl;

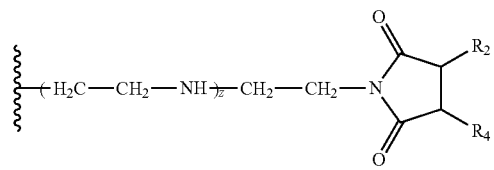

and wherein $R_2$ may vary independently and has the following formula III:

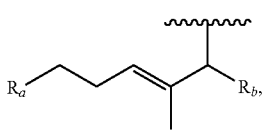

and wherein $R_a$ and $R_b$ are independently a $(C_3-C_{15})$alkyl, cycloalkyl or cycloalkenyl;

and wherein $R_4$ is selected from the group consisting of hydrogen, $(C_1-C_6)$alkyl, $(C_1-C_6)$alkenyl, $(C_3-C_7)$cycloalkyl, and $-(C_2-C_9)$heterocyclyl; wherein said $(C_1-C_6)$alkyl, $(C_1-C_6)$alkenyl, $-(C_3-C_7)$cycloalkyl, and $-(C_2-C_9)$heterocyclyl substituents may be optionally substituted by one to three moieties independently selected from the group consisting of hydrogen, halogen, hydroxyl, $-(C_1-C_{16})$alkyl, $(C_1-C_{16})$alkenyl, $-CN$, $-NR_8R_9$, $-OR_8$, $-(C_3-C_7)$cycloalkyl, $-(C_2-C_9)$heterocyclyl, $-CO_2R_{15}$, $-SO_2NR_8R_9$, $NR_{15}SO_2R_{10}$, $-SO_2R_{10}$ and $-CONR_8R_{11}$; wherein $R_8$ and $R_{11}$ of said $-CONR_8R_{11}$ group may be taken together with the atoms to which they are attached to form a $-(C_2-C_9)$heterocyclyl;

and wherein $R_8$ and $R_9$ may each be substituents independently selected from the group consisting of hydrogen, $-(C_1-C_6)$alkyl, $-(C_3-C_7)$cycloalkyl, $-(C_2-C_9)$heterocyclyl and said $-(C_2-C_9)$heterocyclyl group may optionally be interrupted by one to three elements independently selected from the group consisting of $-(C=O)$, $-SO_2$, $-S-$, $-O-$, $-P-$, $-N-$, $-NH-$ and $-NR_{15}$, $-(C_6-C_{10})$aryl, $-(C_1-C_9)$heteroaryl, $COR_{15}$ and $-SO_2R_{15}$; wherein said $-(C_1-C_6)$alkyl, $-(C_3-C_7)$cycloalkyl, $-(C_2-C_9)$heterocyclyl, $-(C_6-C_{10})$aryl, $-(C_1-C_9)$heteroaryl, $-COR_{15}$ and $-SO_2R_{15}R_8$ or $R_9$ substituents may optionally be substituted by one to three moieties independently selected from the group consisting of hydrogen, halogen, -chalcogen, $-CF_3$, $-CN$, $-(C_1-C_6)$alkyl, $-NH(C_1-C_6)$alkyl, $-NH(C_3-C_7)$cycloalkyl, $-NH(C_2-C_9)$heterocyclyl, $-NH(C_6-C_{10})$aryl, $-NH(C_1-C_9)$heteroaryl, $-N((C_1-C_6)$alkyl$)_2$, $-N((C_3-C_7)$cycloalkyl$)_2$-, $-N((C_2-C_9)$heterocyclyl$)_2$, $-N((C_6-C_{10})$aryl$)_2$, $-N((C_1-C_9)$heteroaryl$)_2$, $-O(C_1-C_6)$alkyl, $-O(C_3-C_7)$cycloalkyl, $-O(C_2-C_9)$heterocyclyl, $-O(C_6-C_{10})$aryl, $-O(C_1-C_9)$heteroaryl, $-(C_3-C_7)$cycloalkyl, $-(C_2-C_9)$heterocyclyl, $-CO_2R_{10}$, $SO_2NR_8R_9$, $NR_{15}SO_2R_{10}$, $-SO_2R_{10}$, $-CONH_2$, $-CONHR_{10}$, and $-CONR_{10}R_{11}$; wherein $R_{10}$ and $R_{11}$ of said $-CONR_{10}R_{11}$ group may be taken together with the nitrogen atom to which they are attached to form a $-(C_2-C_9)$ heterocyclyl;

and wherein $R_8$ and $R_9$ may be taken together with the atom(s) to which they are attached to form a $-(C_2-C_9)$ heterocyclyl, wherein said $-(C_2-C_9)$heterocyclyl group may optionally be substituted by one to three moieties selected from the group consisting of hydrogen, halogen, hydroxy, $-CF_3$, $-NO_2$, $-CN$, $-(C_1-C_6)$alkyl, $-(C_2-C_6)$alkenyl, $-(C_2-C_6)$alkynyl, $-C=N-OH$, $-C=N-O((C_1-C_6)$-alkyl), $-NR_{10}R_{11}$, $-OR_{15}$, $-(C_3-C_7)$cycloalkyl, $-(C_2-C_9)$heterocyclyl, $-CO_2R_{15}$, $-CONR_{10}R_{11}$, $-CONR_8R_{11}$, $-SOR_{10}$, $-SO_2R_{10}$, $-SO_2NR_{10}R_{11}$, $-NHCOR_{15}$, $-NR_{15}CONR_{10}R_{11}$, and $-NR_{12}SO_2R_{10}$, wherein said $-(C_2-C_6)$alkenyl and $-(C_2-C_6)$alkynyl moieties of said $-(C_2-C_9)$heterocyclyl group may be optionally substituted by one to three $R_{10}$ groups, and said $-(C_2-C_9)$heterocyclyl group may optionally be interrupted by one to three elements independently selected from the group consisting of $-(C=O)$, $-SO_2$, $-S-$, $-O-$, $-P-$, $-N-$, $-NH-$ and $-NR_{15}$;

and wherein $R_{10}$ is a substituent selected from the group consisting of $-(C_1-C_6)$alkyl, $-(C_3-C_7)$cycloalkyl, $-(C_2-C_9)$heterocyclyl, $-(C_6-C_{10})$aryl, and $-(C_1-C_9)$ heteroaryl; wherein said $-(C_1-C_6)$alkyl, $-(C_3-C_7)$cycloalkyl, $-(C_2-C_9)$heterocyclyl, $-(C_6-C_{10})$aryl, and $-(C_1-C_9)$ heteroaryl $R_{10}$ substituents may optionally be substituted by one to three moieties independently selected from the group consisting of hydrogen, halogen, hydroxy, $-CN$, $-(C_1-C_6)$alkyl, $-NR_{15}$, and $-O(C_1-C_6)$alkyl;

and wherein $R_{11}$ is a substituent selected from the group consisting of hydrogen, $-(C_1-C_6)$alkyl, $-(C_3-C_7)$cycloalkyl, $-(C_2-C_9)$heterocyclyl, $-(C_6-C_{10})$aryl, and $-(C_1-C_9)$ heteroaryl; wherein said $-(C_1-C_6)$alkyl, $-(C_3-C_7)$cycloalkyl, $-(C_2-C_9)$heterocyclyl, $-(C_6-C_{10})$aryl, and $-(C_1-C_9)$ heteroaryl $R_{11}$ radicals may optionally be substituted by one to three moieties independently selected from the group consisting of hydrogen, halogen, hydroxy, $-CN$, $-(C_1-C_6)$alkyl, $-NH_2$, $-NHR_{12}$, $-N(R_{12})_2$, $-OR_{12}$, $-(C_3-C_7)$cycloalkyl, $-(C_2-C_9)$heterocyclyl, $-CO_2R_{13}$, $-CONH_2$, $-CONHR_{13}$, and $-CONR_{13}R_{14}$; wherein $R_{13}$ and $R_{14}$ of $-CONR_{13}R_{14}$ may be taken together with the nitrogen atom to which they are attached to form a $-(C_2-C_9)$heterocyclyl;

and wherein $R_{12}$ and $R_{13}$ may each be independently selected from the group consisting of hydrogen and —$(C_1$-$C_6)$alkyl;

and wherein $R_{14}$ may be selected from the group consisting of hydrogen and —$(C_1$-$C_6)$alkyl;

and wherein $R_{15}$ may be a substituent selected from the group consisting of hydrogen, —$(C_1$-$C_6)$alkyl, —$(C_3$-$C_7)$cycloalkyl, —$(C_2$-$C_9)$heterocyclyl, —$(C_6$-$C_{10})$aryl, and —$(C_1$-$C_9)$heteroaryl; wherein said —$(C_1$-$C_6)$alkyl, —$(C_3$-$C_7)$cycloalkyl, —$(C_2$-$C_9)$heterocyclyl, —$(C_6$-$C_{10})$aryl, and —$(C_1$-$C_9)$heteroaryl $R_{15}$ substituent may optionally be substituted by one to three moieties independently selected from the group consisting of hydrogen, halogen, —$CF_3$, —$CN$, —$(C_1$-$C_6)$alkyl, —$NH(C_1$-$C_6)$alkyl, —$NH(C_3$-$C_7)$cycloalkyl, —$NH(C_2$-$C_9)$heterocyclyl, —$NH(C_6$-$C_{10})$aryl, —$NH(C_1$-$C_9)$heteroaryl, —$N((C_1$-$C_6)$alkyl$)_2$, —$N((C_3$-$C_7)$cycloalkyl$)_2$, —$N((C_2$-$C_9)$heterocyclyl$)_2$, —$N((C_6$-$C_{10})$aryl$)_2$, —$N((C_1$-$C_9)$heteroaryl$)_2$, —$O(C_1$-$C_6)$alkyl, —$O(C_3$-$C_7)$cycloalkyl, —$O(C_2$-$C_9)$heterocyclyl, —$O(C_6$-$C_{10})$aryl, —$O(C_1$-$C_9)$heteroaryl, —$(C_3$-$C_7)$cycloalkyl, —$(C_2$-$C_9)$heterocyclyl, —$CO_2R_{10}$, —$CONH_2$, —$CONHR_{10}$, and —$CONR_{10}R_{11}$;

and wherein $R_{10}$ and $R_{11}$ of said —$CONR_{10}R_{11}$ group may be taken together with the atoms which they are attached to form a —$(C_2$-$C_9)$ heterocyclyl.

In some embodiments, $R_2$ may represent the formula IV:

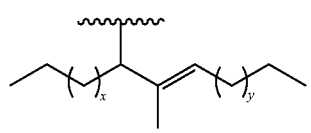

IV wherein x and y must each at least be 1 and (x+y) is 8, 10, 12, 14, 16 or 18.

In some embodiments, $R_1$ may represent the formula II:

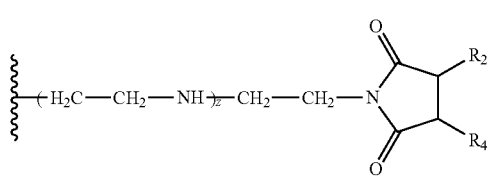

II

In other embodiments, $R_1$ may represent $C_1$-$C_6$ alkyl.
In other embodiments, $R_4$ may represent a $C_1$-$C_6$ alkyl.

The following is a non-limiting list of compounds according to the present invention:
(5-methylnonadec-5-en-4-yl)pyrrolidine-2,5-dione;
(5-methylnonadec-6-en-5-yl)pyrrolidine-2,5-dione;
(7-methylnonadec-7-en-6-yl)pyrrolidine-2,5-dione;
(8-methylnonadec-8-en-7-yl)pyrrolidine-2,5-dione;
(9-methylnonadec-9-en-8-yl)pyrrolidine-2,5-dione;
(10-methylnonadec-10-en-9-yl)pyrrolidine-2,5-dione;
(9-methylnonadec-8-en-10-yl)pyrrolidine-2,5-dione;
(8-methylnonadec-7-en-9-yl)pyrrolidine-2,5-dione;
(7-methylnonadec-6-en-8-yl)pyrrolidine-2,5-dione;
(6-methylnonadec-5-en-7-yl)pyrrolidine-2,5-dione;
(5-methylnonadec-4-en-6-yl)pyrrolidine-2,5-dione;
(4-methylnonadec-3-en-5-yl)pyrrolidine-2,5-dione;
(3-methylnonadec-2-en-4-yl)pyrrolidine-2,5-dione;
(2,2'-(ethane-1,2-diylbis(azanediyl))bis(ethane-2,1-diyl))bis(3-(8-methylnonadec-8-en-7-yl)pyrrolidine-2,5-dione);
(3-methylhenicos-2-en-4-yl)pyrrolidine-2,5-dione;
(4-methylhenicos-3-en-5-yl)pyrrolidine-2,5-dione;
(5-methylhenicos-4-en-6-yl)pyrrolidine-2,5-dione;
(6-methylhenicos-5-en-7-yl)pyrrolidine-2,5-dione;
(7-methylhenicos-6-en-8-yl)pyrrolidine-2,5-dione;
(8-methylhenicos-7-en-9-yl)pyrrolidine-2,5-dione;
(9-methylhenicos-8-en-10-yl)pyrrolidine-2,5-dione;
(10-methylhenicos-9-en-11-yl)pyrrolidine-2,5-dione;
(11-methylhenicos-11-en-10-yl)pyrrolidine-2,5-dione;
(10-methylhenicos-10-en-9-yl)pyrrolidine-2,5-dione;
(9-methylhenicos-9-en-8-yl)pyrrolidine-2,5-dione;
(8-methylhenicos-8-en-7-yl)pyrrolidine-2,5-dione;
(7-methylhenicos-7-en-6-yl)pyrrolidine-2,5-dione;
(6-methylhenicos-6-en-5-yl)pyrrolidine-2,5-dione;
(5-methylhenicos-5-en-4-yl)pyrrolidine-2,5-dione;
(2,2'-(ethane-1,2-diylbis(azanediyl))bis(ethane-2,1-diyl))bis(3-(5-methylhenicos-5-en-4-yl)pyrrolidine-2,5-dione);
(5-methyltricos-5-en-4-yl)pyrrolidine-2,5-dione;
(6-methyltricos-6-en-5-yl)pyrrolidine-2,5-dione;
(7-methyltricos-7-en-6-yl)pyrrolidine-2,5-dione;
(8-methyltricos-8-en-7-yl)pyrrolidine-2,5-dione;
(9-methyltricos-9-en-8-yl)pyrrolidine-2,5-dione;
(10-methyltricos-10-en-9-yl)pyrrolidine-2,5-dione;
(11-methyltricos-11-en-10-yl)pyrrolidine-2,5-dione;
(12-methyltricos-12-en-11-yl)pyrrolidine-2,5-dione;
(11-methyltricos-10-en-12-yl)pyrrolidine-2,5-dione;
(10-methyltricos-9-en-11-yl)pyrrolidine-2,5-dione;
(9-methyltricos-8-en-10-yl)pyrrolidine-2,5-dione;
(8-methyltricos-7-en-9-yl)pyrrolidine-2,5-dione;
(7-methyltricos-6-en-8-yl)pyrrolidine-2,5-dione;
(6-methyltricos-5-en-7-yl)pyrrolidine-2,5-dione;
(5-methyltricos-4-en-6-yl)pyrrolidine-2,5-dione;
(4-methyltricos-3-en-5-yl)pyrrolidine-2,5-dione;
(3-methyltricos-2-en-4-yl)pyrrolidine-2,5-dione;
(2,2'-(ethane-1,2-diylbis(azanediyl))bis(ethane-2,1-diyl))bis(3-(5-methyltricos-5-en-4-yl)pyrrolidine-2,5-dione);
(3-methylpentacos-2-en-4-yl)pyrrolidine-2,5-dione;
(4-methylpentacos-3-en-5-yl)pyrrolidine-2,5-dione;
(5-methylpentacos-4-en-6-yl)pyrrolidine-2,5-dione;
(6-methylpentacos-5-en-7-yl)pyrrolidine-2,5-dione;
(7-methylpentacos-6-en-8-yl)pyrrolidine-2,5-dione;
(8-methylpentacos-7-en-9-yl)pyrrolidine-2,5-dione;
(9-methylpentacos-8-en-10-yl)pyrrolidine-2,5-dione;
(10-methylpentacos-9-en-11-yl)pyrrolidine-2,5-dione;
(11-methyl pentacos-10-en-12-yl)pyrrolidine-2,5-dione;
(12-methylpentacos-11-en-13-yl)pyrrolidine-2,5-dione;
(13-methylpentacos-13-en-12-yl)pyrrolidine-2,5-dione;
(12-methylpentacos-12-en-11-yl)pyrrolidine-2,5-dione;
(11-methyl pentacos-11-en-10-yl)pyrrolidine-2,5-dione;
(10-methylpentacos-10-en-9-yl)pyrrolidine-2,5-dione;
(9-methylpentacos-9-en-8-yl)pyrrolidine-2,5-dione;
(8-methylpentacos-8-en-7-yl)pyrrolidine-2,5-dione;
(7-methylpentacos-7-en-6-yl)pyrrolidine-2,5-dione;
(6-methylpentacos-6-en-5-yl)pyrrolidine-2,5-dione;
(5-methylpentacos-5-en-4-yl)pyrrolidine-2,5-dione;
(2,2'-(ethane-1,2-diylbis(azanediyl))bis(ethane-2,1-diyl))bis(3-(7-methylpentacos-7-en-6-yl)pyrrolidine-2,5-dione);
and a tribologically acceptable salt or solvate thereof.

In yet another embodiment a lubricant composition may comprise one or more compounds according to formula I, or a tribologically acceptable salt or solvate thereof.

In yet another embodiment, a lubricant additive composition may comprise one or more compounds according to formula I, or a tribologically acceptable salt or solvate thereof.

In another embodiment a lubricant composition may comprise a) a major amount of a base oil; and b) a minor amount of an additive composition comprising one or more compounds of formula I, or a tribologically acceptable salt or solvate thereof.

In another embodiment a lubricant composition may comprise between about 1 and 10 wt. % of a compound of formula I, or a tribologically acceptable salt or solvate thereof.

In still another embodiment the lubricant and lubricant additive compositions comprising one or more compounds of formula I, or a tribologically acceptable salt or solvate thereof, may further comprise an oil-soluble ashless dispersant selected from the group consisting of: a succinimide dispersant, a succinic ester dispersant, a succininic ester-amide dispersant, a Mannich base dispersant, phosphorylated forms thereof, and boronated forms thereof.

In still another embodiment the lubricant and lubricant additive compositions comprising one or more compounds of formula I, or a tribologically acceptable salt or solvate thereof, may further comprise one or more of the following: an air expulsion additive, an antioxidant, a corrosion inhibitor, a foam inhibitor, a metallic detergent, an organic phosphorus compound, a seal-swell agent, a viscosity index improver, and an extreme pressure additive.

In yet another embodiment, a lubricant additive may comprise a reaction product obtained by the process of a) combining a tri-substituted internal olefin, wherein each olefin comprises from about 12 to about 36 carbon atoms, and maleic anhydride at a sufficient elevated temperature for a sufficient amount of time to provide a maleated product; (b) aminating and neutralizing the maleated product with an effective amount of a compound containing basic nitrogen at an elevated temperature; and, optionally, (c) recovering, as a lubricant additive, the reaction product.

In yet another embodiment a lubricant additive may be the reaction product of a process, wherein the ratio of tri-substituted internal olefin to maleic anhydride is about 0.5 to about 1.

In still another embodiment, a lubricant additive may be the reaction product of a process, wherein the ratio of tri-substituted internal olefin to maleic anhydride is about 0.5 to about 1.5.

Another embodiment of the present invention includes a method of lubricating a machine part comprising lubricating the machine part with a lubricant composition including a compound of formula I, or a tribologically acceptable salt or solvate thereof.

In another embodiment, a method of lubricating a machine part with a lubricant composition including a compound of formula I, or a tribologically acceptable salt or solvate thereof, may comprise lubricating the machine part with a lubricant composition including a compound of formula I, or a tribologically acceptable salt or solvate thereof, present in the lubricant composition in an amount between about 1 and 10 wt. %.

In yet another embodiment a method of lubricating a machine part with a compound of formula I further comprises lubricating machine parts selected from the group consisting of a gear, an axle, a differential, an engine, a crankshaft, a transmission, or a clutch.

In yet another embodiment a method of lubricating a transmission with a compound of formula I further comprises lubricating transmissions selected from the group consisting of an automatic transmission, a manual transmission, an automated manual transmission, a semi-automatic transmission, a dual clutch transmission, a continuously variable transmission, and a toroidal transmission.

In yet another embodiment a method of lubricating a clutch component with a compound of formula I further comprises lubricating clutch components selected from the group consisting of a continuously slipping torque converter clutch, a slipping torque converter clutch, a lock-up torque converter clutch, a starting clutch, one or more shifting clutches, or an electronically controlled converter clutch.

In yet another embodiment a method of lubricating a gear with a compound of formula I further comprises lubricating gears selected from the group consisting of an automotive gear, a stationary gearbox, and an axle.

In yet another embodiment a method of lubricating a gear with a compound of formula I further comprises lubricating gears selected from the group consisting of a hypoid gear, a spur gear, a helical gear, a bevel gear, a worm gear, a rack and pinion gear, a planetary gear set, and an involute gear.

In yet another embodiment a method of lubricating a differential with a compound of formula I further comprises lubricating differentials selected from the group consisting of a straight differential, a turning differential, a limited slip differential, a clutch-type limited slip differential, and a locking differential.

In yet another embodiment a method of lubricating an engine with a compound of formula I further comprises lubricating an engine selected from the group consisting of an internal combustion engine, a rotary engine, a gas turbine engine, a four-stroke engine, and a two-stroke engine.

In yet another embodiment, a method of lubricating an engine with a compound of formula I may further comprise lubricating engine parts selected from the group consisting of a piston, a bearing, a crankshaft, and/or a camshaft.

Another embodiment includes a method for testing lubricant properties of a composition using a testing apparatus comprising lubricating said testing apparatus with a lubricant composition comprising a compound of the formula I, or a tribologically acceptable salt or solvate thereof. The testing apparatus may include a Brookfield viscometer, any Vickers Test apparatus, an SAE No. 2 friction test machine, an electric motor-driven Hydra-Matic 4L60-E automatic transmission, ASTM D 471 or D 676 Elastomer Compatibility test equipment, NOACK volatility procedure machine, any test apparatus necessary for ASTM D 2882, D 5182, D 4172, D3233, and D2782 Wear Procedures, ASTM Foaming Procedure apparatus, test apparatus necessary for ASTM D 130 Copper Corrosion test, test equipment specified by the International Harvester Procedure Method BT-9 Rust Control test, test apparatus required by ASTM D 892 Foaming test, test apparatus required by ASTM D 4998 Gear Anti-Wear Performance test, Link M1158 Oil/Friction Machine, L-33-1 Test Apparatus, L-37 Test Apparatus, L-42 Test Apparatus, L-60-1 Test Apparatus, Strama 4-Square Electric Motor-Driven Procedure Machine, FZG Test Apparatus and parts, SSP-180 Procedure Machine, test apparatus for ASTM D 5579 High Temperature Cyclic Durability Procedure, Sauer-Danfoss Series 22 or Series 90 Axial Piston Pump, John Deere Synchro-Plus transmission, an SRV-friction wear tester, a 4-ball test apparatus, an LFW-1 test apparatus, a sprag clutch overrunning wear test (SCOWT) apparatus, API CJ-4 engine tests, L-33 Moisture Corrosion Test, High-Temperature Cyclic Durability Test (ASTM D 5579), 288-hour VE engine oil performance test, L-38 standard lubricant test, Denison P46 Piston Pump Test Stand, Sundstrand Dynamic Corrosion Test Stand, a block-on-ring test apparatus, and any test apparatus required for performing test analysis under Mercon®, Mercon® V, Dexron® III, Dexron® III-H, Caterpillar® TO-4, Allison® C-4, JASO, GF-4, GF-5, MIL-E, MIL-L, and Sequences II through VIII.

In yet another embodiment, a method for improving the low temperature viscometric properties of a lubricating fluid may comprise including in a lubricating fluid an effective amount of one or more compounds of formula I, or a tribologically acceptable salt or solvate thereof.

In still another embodiment a method for improving the low temperature viscometric properties of a lubricating fluid while lubricating an automotive component requiring lubrication, may comprise: 1) adding a lubricating fluid to an automotive component requiring lubrication, the fluid comprising (a) a base oil, and (b) one or more compounds of formula I, or a tribologically acceptable salt or solvate thereof; and 2) operating the automotive component that contains the fluid, wherein the low temperature viscometric performance of the fluid is improved relative to the performance of a lubricating fluid free of the compound of 1) (b).

In another embodiment the method for improving the low temperature viscometric properties of a lubricating fluid while lubricating an automotive component requiring lubrication may comprise adding a lubricating fluid comprising one or more compounds of formula I, or a tribologically acceptable salt or solvate thereof; in an amount between about 1 and 10 wt. % of the lubricating fluid.

Another embodiment includes a method of making a lubricant additive, comprising: a) combining a tri-substituted internal olefin, wherein each olefin comprises from about 12 to about 36 carbon atoms, and maleic anhydride at a sufficient elevated temperature for a sufficient amount of time to provide a maleated product; (b) aminating and neutralizing the maleated product with an effective amount of a compound containing basic nitrogen at an elevated temperature; and, optionally, (c) recovering, as a lubricant additive, the reaction product.

In yet another embodiment, lubricant compositions may comprise a mixture of: (a) a major amount of a lubricating oil; and (b) a Brookfield viscosity improving effective amount of a compound having the formula I:

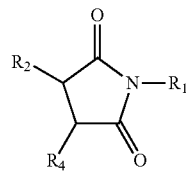

I or a tribologically acceptable salt, solvate, hydrate, or proadditive thereof, wherein $R_1$ is selected from the group consisting of: hydrogen, $-(C_1-C_6)$alkyl, $-(C_1-C_6)$alkenyl, $-(C_3-C_7)$cycloalkyl, $-(C_2-C_9)$heterocyclyl, and a radical having formula II below, where z may be from 1-10;

wherein said $(C_1-C_6)$alkyl, $-(C_1-C_6)$alkenyl, $-(C_3-C_7)$cycloalkyl, and $(C_2-C_9)$heterocyclyl substituents are optionally substituted by one to three moieties independently selected from the group consisting of hydrogen, halogen, hydroxyl, $-(C_1-C_{16})$alkyl, $-(C_1-C_{16})$alkenyl, $-CN$, $-NR_8R_9$, $-OR_8$, $-(C_3-C_7)$cycloalkyl, $-(C_2-C_9)$heterocyclyl, $-CO_2R_{15}$, $-SO_2NR_8R_9$, $-NR_{15}SO_2R_{10}$, $-SO_2R_{10}$ and $-CONR_8R_{11}$; wherein $R_8$ and $R_{11}$ of said $-CONR_8R_{11}$ group may be taken together with the atoms to which they are attached to form a $-(C_2-C_9)$heterocyclyl;

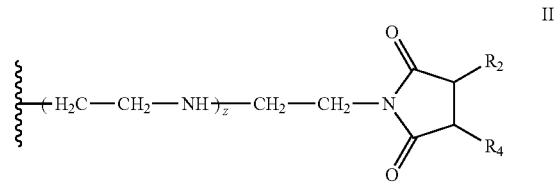

II and wherein $R_2$ may vary independently and has the following formula III:

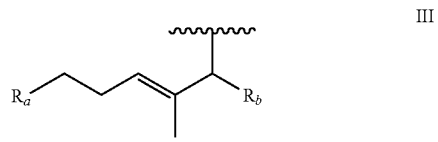

III and wherein $R_a$ and $R_b$ are independently a $(C_3-C_{15})$ alkyl, cycloalkyl or cycloalkenyl;

and wherein $R_4$ is selected from the group consisting of hydrogen, $(C_1-C_6)$alkyl, $(C_1-C_6)$alkenyl, $-(C_3-C_7)$cycloalkyl, and $-(C_2-C_9)$heterocyclyl; wherein said $(C_1-C_6)$alkyl, $(C_1-C_6)$alkenyl, $-(C_3-C_7)$cycloalkyl, and $-(C_2-C_9)$heterocyclyl substituents may be optionally substituted by one to three moieties independently selected from the group consisting of hydrogen, halogen, hydroxyl, $-(C_1-C_{16})$alkyl, $(C_1-C_{16})$alkenyl, $-CN$, $-NR_8R_9$, $-OR_8$, $-(C_3-C_7)$cycloalkyl, $-(C_2-C_9)$heterocyclyl, $-CO_2R_{15}$, $-SO_2NR_8R_9$, $NR_{15}SO_2R_{10}$, $-SO_2R_{10}$ and $-CONR_8R_{11}$; wherein $R_8$ and $R_{11}$ of said $-CONR_8R_{11}$ group may be taken together with the atoms to which they are attached to form a $-(C_2-C_9)$heterocyclyl;

and wherein $R_8$ and $R_9$ may each be substituents independently selected from the group consisting of hydrogen, $-(C_1-C_6)$alkyl, $-(C_3-C_7)$cycloalkyl, $-(C_2-C_9)$heterocyclyl and said $-(C_2-C_9)$heterocyclyl group may optionally be interrupted by one to three elements independently selected from the group consisting of $-(C=O)$, $-SO_2$, $-S-$, $-O-$, $-P-$, $-N-$, $-NH-$ and $-NR_{15}$, $-(C_6-C_{10})$aryl, $-(C_1-C_9)$heteroaryl, $-COR_{15}$ and $-SO_2R_{15}$; wherein said $-(C_1-C_6)$alkyl, $-(C_3-C_7)$cycloalkyl, $-(C_2-C_9)$heterocyclyl, $-(C_6-C_{10})$aryl, $-(C_1-C_9)$heteroaryl, $-COR_{15}$ and $-SO_2R_{15}R_8$ or $R_9$ substituents may optionally be substituted by one to three moieties independently selected from the group consisting of hydrogen, halogen, -chalcogen, $-CF_3$, $-CN$, $-(C_1-C_6)$alkyl, $-NH(C_1-C_6)$alkyl, $-NH(C_3-C_7)$cycloalkyl, $-NH(C_2-C_9)$heterocyclyl, $-NH(C_6-C_{10})$aryl, $-NH(C_1-C_9)$heteroaryl, $-N((C_1-C_6)$alkyl$)_2$, $-N((C_3-C_7)$cycloalkyl$)_2$-, $-N((C_2-C_9)$heterocyclyl$)_2$, $-N((C_6-C_{10})$aryl$)_2$, $-N((C_1-C_9)$heteroaryl$)_2$, $-O(C_1-C_6)$alkyl, $-O(C_3-C_7)$cycloalkyl, $-O(C_2-C_9)$heterocyclyl, $-O(C_6-C_{10})$aryl, $-O(C_1-C_9)$heteroaryl, $-(C_3-C_7)$cycloalkyl, $-(C_2-C_9)$heterocyclyl, $-CO_2R_{10}$, $SO_2NR_8R_9$, $NR_{15}SO_2R_{10}$, $-SO_2R_{10}$, $-CONH_2$, $-CONHR_{10}$, and $-CONR_{10}R_{11}$; wherein $R_{10}$ and $R_{11}$ of said $-CONR_{10}R_{11}$ group may be taken together with the nitrogen atom to which they are attached to form a $-(C_2-C_9)$ heterocyclyl;

and wherein $R_8$ and $R_9$ may be taken together with the atom(s) to which they are attached to form a $-(C_2-C_9)$ heterocyclyl, wherein said —($C_2$-$C_9$)heterocyclyl group may optionally be substituted by one to three moieties selected from the group consisting of hydrogen, halogen, hydroxy, —$CF_3$, —$NO_2$, —CN, —($C_1$-$C_6$)alkyl, —($C_2$-$C_6$)alkenyl, —($C_2$-$C_6$)alkynyl, —C=N—OH, —C=N—O(($C_1$-$C_6$)-alkyl), —$NR_{10}R_{11}$, —$OR_{15}$, —($C_3$-$C_7$)cycloalkyl, —($C_2$-$C_9$)heterocyclyl, —$CO_2R_{15}$, —$CONR_{10}R_{11}$, —$CONR_8R_{11}$, —$SR_{10}$, —$SOR_{10}$, —$SO_2R_{10}$, —$SO_2NR_{10}R_{11}$, —$NHCOR_{15}$, —$NR_{15}CONR_{10}R_{11}$, and —$NR_{12}SO_2R_{10}$, wherein said —($C_2$-$C_6$)alkenyl and —($C_2$-$C_6$)alkynyl moieties of said —($C_2$-$C_9$)heterocyclyl group may be optionally substituted by one to three $R_{10}$ groups, and said —($C_2$-$C_9$)heterocyclyl group may optionally be interrupted by one to three elements independently selected from the group consisting of —(C=O), —$SO_2$, —S—, —O—, —P—, —N—, —NH— and —$NR_{15}$;

and wherein $R_{10}$ is a substituent selected from the group consisting of —($C_1$-$C_6$)alkyl, —($C_3$-$C_7$)cycloalkyl, —($C_2$-$C_9$)heterocyclyl, —($C_6$-$C_{10}$)aryl, and —($C_1$-$C_9$) heteroaryl; wherein said —($C_1$-$C_6$)alkyl, —($C_3$-$C_7$)cycloalkyl, —($C_2$-$C_9$)heterocyclyl, —($C_6$-$C_{10}$)aryl, and —($C_1$-$C_9$) heteroaryl $R_{10}$ substituents may optionally be substituted by one to three moieties independently selected from the group consisting of hydrogen, halogen, hydroxy, —CN, —($C_1$-$C_6$)alkyl, —$NR_{15}$, and —O($C_1$-$C_6$)alkyl;

and wherein $R_{11}$ is a substituent selected from the group consisting of hydrogen, —($C_1$-$C_6$)alkyl, —($C_3$-$C_7$)cycloalkyl, —($C_2$-$C_9$)heterocyclyl, —($C_6$-$C_{10}$)aryl, and —($C_1$-$C_9$) heteroaryl; wherein said —($C_1$-$C_6$)alkyl, —($C_3$-$C_7$)cycloalkyl, —($C_2$-$C_9$)heterocyclyl, —($C_6$-$C_{10}$)aryl, and —($C_1$-$C_9$) heteroaryl $R_{11}$ radicals may optionally be substituted by one to three moieties independently selected from the group consisting of hydrogen, halogen, hydroxy, —CN, —($C_1$-$C_6$)alkyl, —$NH_2$, —$NHR_{12}$, —N($R_{12}$)$_2$, —$OR_{12}$, —($C_3$-$C_7$)cycloalkyl, —($C_2$-$C_9$)heterocyclyl, —$CO_2R_{13}$, —$CONH_2$, —$CONHR_{13}$, and —$CONR_{13}R_{14}$; wherein $R_{13}$ and $R_{14}$ of —$CONR_{13}R_{14}$ may be taken together with the nitrogen atom to which they are attached to form a —($C_2$-$C_9$)heterocyclyl;

and wherein $R_{12}$ and $R_{13}$ may each be independently selected from the group consisting of hydrogen and —($C_1$-$C_6$)alkyl;

and wherein $R_{14}$ may be selected from the group consisting of hydrogen and —($C_1$-$C_6$)alkyl;

and wherein $R_{15}$ may be a substituent selected from the group consisting of hydrogen, —($C_1$-$C_6$)alkyl, —($C_3$-$C_7$)cycloalkyl, —($C_2$-$C_9$)heterocyclyl, —($C_6$-$C_{10}$)aryl, and —($C_1$-$C_9$)heteroaryl; wherein said —($C_1$-$C_6$)alkyl, —($C_3$-$C_7$)cycloalkyl, —($C_2$-$C_9$)heterocyclyl, —($C_6$-$C_{10}$)aryl, and —($C_1$-$C_9$)heteroaryl $R_{15}$ substituent may optionally be substituted by one to three moieties independently selected from the group consisting of hydrogen, halogen, —$CF_3$, —CN, —($C_1$-$C_6$)alkyl, —NH($C_1$-$C_6$)alkyl, —NH($C_3$-$C_7$)cycloalkyl, —NH($C_2$-$C_9$)heterocycyl, —NH($C_6$-$C_{10}$)aryl, —NH($C_1$-$C_9$) heteroaryl, —N(($C_1$-$C_6$)alkyl)$_2$, —N(($C_3$-$C_7$cycloalkyl)$_2$-, —N(($C_2$-$C_9$)heterocyclyl)$_2$, —N(($C_6$-$C_{10}$)aryl)$_2$, —N(($C_1$-$C_9$)heteroaryl)$_2$, —O($C_1$-$C_6$)alkyl, —O($C_3$-$C_7$)cycloalkyl, —O($C_2$-$C_9$)heterocyclyl, —O($C_6$-$C_{10}$)aryl, —O($C_1$-$C_9$)heteroaryl, —($C_3$-$C_7$)cycloalkyl, —($C_2$-$C_9$)heterocyclyl, —$CO_2R_{10}$, —$CONH_2$, —$CONHR_{10}$, and —$CONR_{10}R_{11}$;

and wherein $R_{10}$ and $R_{11}$ of said —$CONR_{10}R_{11}$ group may be taken together with the atoms which they are attached to to form a —($C_2$-$C_9$) heterocyclyl.

In another embodiment, a lubricant composition comprises a compound of formula I having an $R_2$ represented by formula IV:

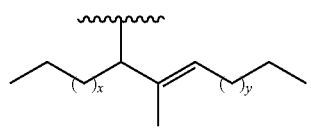

wherein x and y must each at least be 1 and (x+y) is 8, 10, 12, 14, 16 or 18.

In yet another embodiment, a lubricant composition comprises a compound of formula I having an $R_1$ represented by the formula:

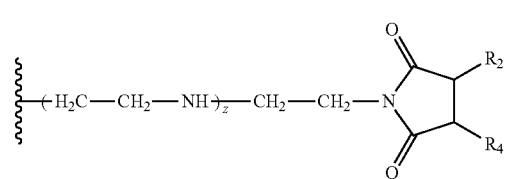

In yet another embodiment, a lubricant composition comprises a compound of formula I having an $R_1$ of $C_1$-$C_6$ alkyl.

In yet another embodiment, a lubricant composition comprises a compound of formula I having an $R_4$ of $C_1$-$C_6$ alkyl.

In yet another embodiment lubricant compositions may comprise a mixture of: (a) a major amount of a lubricating oil; and (b) a Brookfield viscosity improving effective amount of a compound having the formula I, wherein the compound of formula I is selected from the group consisting of:
(5-methylnonadec-5-en-4-yl)pyrrolidine-2,5-dione;
(6-methylnonadec-6-en-5-yl)pyrrolidine-2,5-dione;
(7-methylnonadec-7-en-6-yl)pyrrolidine-2,5-dione;
(8-methylnonadec-8-en-7-yl)pyrrolidine-2,5-dione;
(9-methylnonadec-9-en-8-yl)pyrrolidine-2,5-dione;
(10-methylnonadec-10-en-9-yl)pyrrolidine-2,5-dione;
(9-methylnonadec-8-en-10-yl)pyrrolidine-2,5-dione;
(8-methylnonadec-7-en-9-yl)pyrrolidine-2,5-dione;
(7-methylnonadec-6-en-8-yl)pyrrolidine-2,5-dione;
(6-methylnonadec-5-en-7-yl)pyrrolidine-2,5-dione;
(5-methylnonadec-4-en-6-yl)pyrrolidine-2,5-dione;
(4-methylnonadec-3-en-5-yl)pyrrolidine-2,5-dione;
(3-methylnonadec-2-en-4-yl)pyrrolidine-2,5-dione;
(2,2'-(ethane-1,2-diylbis(azanediyl))bis(ethane-2,1-diyl))bis (3-(8-methylnonadec-8-en-7-yl)pyrrolidine-2,5-dione);
(3-methylhenicos-2-en-4-yl)pyrrolidine-2,5-dione;
(4-methylhenicos-3-en-5-yl)pyrrolidine-2,5-dione;
(5-methylhenicos-4-en-6-yl)pyrrolidine-2,5-dione;
(6-methylhenicos-5-en-7-yl)pyrrolidine-2,5-dione;
(7-methylhenicos-6-en-8-yl)pyrrolidine-2,5-dione;
(8-methylhenicos-7-en-9-yl)pyrrolidine-2,5-dione;
(9-methylhenicos-8-en-10-yl)pyrrolidine-2,5-dione;
(10-methylhenicos-9-en-11-yl)pyrrolidine-2,5-dione;
(11-methylhenicos-11-en-10-yl)pyrrolidine-2,5-dione;
(10-methylhenicos-10-en-9-yl)pyrrolidine-2,5-dione;
(9-methylhenicos-9-en-8-yl)pyrrolidine-2,5-dione;
(8-methylhenicos-8-en-7-yl)pyrrolidine-2,5-dione;

(7-methylhenicos-7-en-6-yl)pyrrolidine-2,5-dione;
(6-methylhenicos-6-en-5-yl)pyrrolidine-2,5-dione;
(5-methylhenicos-5-en-4-yl)pyrrolidine-2,5-dione;
(2,2'-(ethane-1,2-diylbis(azanediyl))bis(ethane-2,1-diyl))bis
  (3-(5-methylhenicos-5-en-4-yl)pyrrolidine-2,5-dione);
(5-methyltricos-5-en-4-yl)pyrrolidine-2,5-dione;
(6-methyltricos-6-en-5-yl)pyrrolidine-2,5-dione;
(7-methyltricos-7-en-6-yl)pyrrolidine-2,5-dione;
(8-methyltricos-8-en-7-yl)pyrrolidine-2,5-dione;
(9-methyltricos-9-en-8-yl)pyrrolidine-2,5-dione;
(10-methyltricos-10-en-9-yl)pyrrolidine-2,5-dione;
(11-methyltricos-11-en-10-yl)pyrrolidine-2,5-dione;
(12-methyltricos-12-en-11-yl)pyrrolidine-2,5-dione;
(11-methyltricos-10-en-12-yl)pyrrolidine-2,5-dione;
(10-methyltricos-9-en-11-yl)pyrrolidine-2,5-dione;
(9-methyltricos-8-en-10-yl)pyrrolidine-2,5-dione;
(8-methyltricos-7-en-9-yl)pyrrolidine-2,5-dione;
(7-methyltricos-6-en-8-yl)pyrrolidine-2,5-dione;
(6-methyltricos-5-en-7-yl)pyrrolidine-2,5-dione;
(5-methyltricos-4-en-6-yl)pyrrolidine-2,5-dione;
(4-methyltricos-3-en-5-yl)pyrrolidine-2,5-dione;
(3-methyltricos-2-en-4-yl)pyrrolidine-2,5-dione;
(2,2'-(ethane-1,2-diylbis(azanediyl))bis(ethane-2,1-diyl))bis
  (3-(5-methyltricos-5-en-4-yl)pyrrolidine-2,5-dione);
(3-methylpentacos-2-en-4-yl)pyrrolidine-2,5-dione;
(4-methylpentacos-3-en-5-yl)pyrrolidine-2,5-dione;
(5-methylpentacos-4-en-6-yl)pyrrolidine-2,5-dione;
(6-methylpentacos-5-en-7-yl)pyrrolidine-2,5-dione;
(7-methylpentacos-6-en-8-yl)pyrrolidine-2,5-dione;
(8-methylpentacos-7-en-9-yl)pyrrolidine-2,5-dione;
(9-methylpentacos-8-en-10-yl)pyrrolidine-2,5-dione;
(10-methylpentacos-9-en-11-yl)pyrrolidine-2,5-dione;
(11-methyl pentacos-10-en-12-yl)pyrrolidine-2,5-dione;
(12-methylpentacos-11-en-13-yl)pyrrolidine-2,5-dione;
(13-methyl pentacos-13-en-12-yl)pyrrolidine-2,5-dione;
(12-methylpentacos-12-en-11-yl)pyrrolidine-2,5-dione;
(11-methyl pentacos-11-en-10-yl)pyrrolidine-2,5-dione;
(10-methyl pentacos-10-en-9-yl)pyrrolidine-2,5-dione;
(9-methylpentacos-9-en-8-yl)pyrrolidine-2,5-dione;
(8-methylpentacos-8-en-7-yl)pyrrolidine-2,5-dione;
(7-methylpentacos-7-en-6-yl)pyrrolidine-2,5-dione;
(6-methylpentacos-6-en-5-yl)pyrrolidine-2,5-dione;
(5-methylpentacos-5-en-4-yl)pyrrolidine-2,5-dione;
(2,2'-(ethane-1,2-diylbis(azanediyl))bis(ethane-2,1-diyl))bis
  (3-(7-methylpentacos-7-en-6-yl)pyrrolidine-2,5-dione);
and a tribologically acceptable salt or solvate thereof.

In yet another embodiment, the lubricant composition comprises a Brookfield improving effective amount of a compound of formula I wherein said lubricant composition comprises a BV −40 of less than about 10,000 cP.

In another embodiment, the lubricant composition comprises a Brookfield viscosity improving effective amount of a compound having the formula I, or a tribologically acceptable salt, solvate, hydrate, or proadditive thereof, wherein the Brookfield viscosity improving effective amount comprises between about 1 and 10 wt. % of the lubricant composition.

In another embodiment, a reaction product, or a tribologically acceptable salt or solvate thereof, may be obtained by reacting a $C_{10}$-$C_{36}$ vinylidene olefin with maleic acid, anhydride, or ester to provide a hydrocarbon-substituted succinic acid, anhydride or ester and aminating the hydrocarbon-substituted succinic acid, anhydride or ester with an effective amount of a compound containing basic nitrogen.

In some embodiments of the reaction product the $C_{10}$-$C_{36}$ vinylidene olefin may represent the formula V:

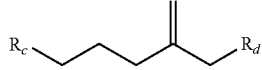

wherein $R_c$ and $R_d$ are independently a $(C_3$-$C_{15})$ alkyl, cycloalkyl or cycloalkenyl.

In some embodiments, the reaction product may be selected from the group consisting of:
(5-methylnonadec-5-en-4-yl)pyrrolidine-2,5-dione;
(6-methylnonadec-6-en-5-yl)pyrrolidine-2,5-dione;
(7-methylnonadec-7-en-6-yl)pyrrolidine-2,5-dione;
(8-methylnonadec-8-en-7-yl)pyrrolidine-2,5-dione;
(9-methylnonadec-9-en-8-yl)pyrrolidine-2,5-dione;
(10-methylnonadec-10-en-9-yl)pyrrolidine-2,5-dione;
(9-methylnonadec-8-en-10-yl)pyrrolidine-2,5-dione;
(8-methylnonadec-7-en-9-yl)pyrrolidine-2,5-dione;
(7-methylnonadec-6-en-8-yl)pyrrolidine-2,5-dione;
(6-methylnonadec-5-en-7-yl)pyrrolidine-2,5-dione;
(5-methylnonadec-4-en-6-yl)pyrrolidine-2,5-dione;
(4-methylnonadec-3-en-5-yl)pyrrolidine-2,5-dione;
(3-methylnonadec-2-en-4-yl)pyrrolidine-2,5-dione;
(2,2'-(ethane-1,2-diylbis(azanediyl))bis(ethane-2,1-diyl))bis
  (3-(8-methylnonadec-8-en-7-yl)pyrrolidine-2,5-dione);
(3-methylhenicos-2-en-4-yl)pyrrolidine-2,5-dione;
(4-methylhenicos-3-en-5-yl)pyrrolidine-2,5-dione;
(5-methylhenicos-4-en-6-yl)pyrrolidine-2,5-dione;
(6-methylhenicos-5-en-7-yl)pyrrolidine-2,5-dione;
(7-methylhenicos-6-en-8-yl)pyrrolidine-2,5-dione;
(8-methylhenicos-7-en-9-yl)pyrrolidine-2,5-dione;
(9-methylhenicos-8-en-10-yl)pyrrolidine-2,5-dione;
(10-methylhenicos-9-en-11-yl)pyrrolidine-2,5-dione;
(11-methylhenicos-11-en-10-yl)pyrrolidine-2,5-dione;
(10-methylhenicos-10-en-9-yl)pyrrolidine-2,5-dione;
(9-methylhenicos-9-en-8-yl)pyrrolidine-2,5-dione;
(8-methylhenicos-8-en-7-yl)pyrrolidine-2,5-dione;
(7-methylhenicos-7-en-6-yl)pyrrolidine-2,5-dione;
(6-methylhenicos-6-en-5-yl)pyrrolidine-2,5-dione;
(5-methylhenicos-5-en-4-yl)pyrrolidine-2,5-dione;
(2,2'-(ethane-1,2-diylbis(azanediyl))bis(ethane-2,1-diyl))bis
  (3-(5-methylhenicos-5-en-4-yl)pyrrolidine-2,5-dione);
(5-methyltricos-5-en-4-yl)pyrrolidine-2,5-dione;
(6-methyltricos-6-en-5-yl)pyrrolidine-2,5-dione;
(7-methyltricos-7-en-6-yl)pyrrolidine-2,5-dione;
(8-methyltricos-8-en-7-yl)pyrrolidine-2,5-dione;
(9-methyltricos-9-en-8-yl)pyrrolidine-2,5-dione;
(10-methyltricos-10-en-9-yl)pyrrolidine-2,5-dione;
(11-methyltricos-11-en-10-yl)pyrrolidine-2,5-dione;
(12-methyltricos-12-en-11-yl)pyrrolidine-2,5-dione;
(11-methyltricos-10-en-12-yl)pyrrolidine-2,5-dione;
(10-methyltricos-9-en-11-yl)pyrrolidine-2,5-dione;
(9-methyltricos-8-en-10-yl)pyrrolidine-2,5-dione;
(8-methyltricos-7-en-9-yl)pyrrolidine-2,5-dione;
(7-methyltricos-6-en-8-yl)pyrrolidine-2,5-dione;
(6-methyltricos-5-en-7-yl)pyrrolidine-2,5-dione;
(5-methyltricos-4-en-6-yl)pyrrolidine-2,5-dione;
(4-methyltricos-3-en-5-yl)pyrrolidine-2,5-dione;
(3-methyltricos-2-en-4-ylpyrrolidine-2,5-dione;
(2,2'-(ethane-1,2-diylbis(azanediyl))bis(ethane-2,1-diyl))bis
  (3-(5-methyltricos-5-en-4-yl)pyrrolidine-2,5-dione);
(3-methylpentacos-2-en-4-yl)pyrrolidine-2,5-dione;
(4-methylpentacos-3-en-5-yl)pyrrolidine-2,5-dione;
(5-methylpentacos-4-en-6-yl)pyrrolidine-2,5-dione;

(6-methylpentacos-5-en-7-yl)pyrrolidine-2,5-dione;
(7-methylpentacos-6-en-8-yl)pyrrolidine-2,5-dione;
(8-methylpentacos-7-en-9-yl)pyrrolidine-2,5-dione;
(9-methylpentacos-8-en-10-yl)pyrrolidine-2,5-dione;
(10-methylpentacos-9-en-11-yl)pyrrolidine-2,5-dione;
(11-methylpentacos-10-en-12-yl)pyrrolidine-2,5-dione;
(12-methylpentacos-11-en-13-yl)pyrrolidine-2,5-dione;
(13-methylpentacos-13-en-12-yl)pyrrolidine-2,5-dione;
(12-methylpentacos-12-en-11-yl)pyrrolidine-2,5-dione;
(11-methylpentacos-11-en-10-yl)pyrrolidine-2,5-dione;
(10-methylpentacos-10-en-9-yl)pyrrolidine-2,5-dione;
(9-methylpentacos-9-en-8-yl)pyrrolidine-2,5-dione;
(8-methylpentacos-8-en-7-yl)pyrrolidine-2,5-dione;
(7-methylpentacos-7-en-6-yl)pyrrolidine-2,5-dione;
(6-methylpentacos-6-en-5-yl)pyrrolidine-2,5-dione;
(5-methylpentacos-5-en-4-yl)pyrrolidine-2,5-dione;
(2,2'-(ethane-1,2-diylbis(azanediyl))bis(ethane-2,1-diyl))bis(3-(7-methylpentacos-7-en-6-yl)pyrrolidine-2,5-dione);
and a tribologically acceptable salt or solvate thereof.

In some embodiments, a lubricant composition may comprise one or more said reaction products, or a tribologically acceptable salt or solvate thereof.

In some embodiments, a lubricant additive composition may comprise one or more said reaction products, or a tribologically acceptable salt or solvate thereof.

In some embodiments, a lubricant composition may comprise: a) a major amount of a base oil; and b) a minor amount of an additive composition comprising one or more said reaction products, or a tribologically acceptable salt or solvate thereof.

In some embodiments, the lubricant composition may comprise one or more said reaction products, or a tribologically acceptable salt or solvate thereof present said lubricant composition in an amount between about 1 and 10 wt. %.

In some embodiments, the lubricant composition may further comprise an oil-soluble ashless dispersant selected from the group consisting of: a succinimide dispersant, a succinic ester dispersant, a succininic ester-amide dispersant, a Mannich base dispersant, phosphorylated forms thereof, and boronated forms thereof.

In some embodiments, the lubricant composition may further comprise one or more of the following: an air expulsion additive, an antioxidant, a corrosion inhibitor, a foam inhibitor, a metallic detergent, an organic phosphorus compound, a seal-swell agent, a viscosity index improver, and an extreme pressure additive.

In some embodiments, a lubricant additive may comprise a reaction product obtained by the process of: a) reacting a $C_{10}$-$C_{36}$ vinylidene olefin with maleic acid, anhydride, or ester to provide a hydrocarbon-substituted succinic acid, anhydride or ester; and b) aminating the said hydrocarbon-substituted succinic acid, anhydride or ester with an effective amount of a compound containing basic nitrogen.

In some embodiments, the ratio of vinylidene olefin to maleic anhydride is about 0.5 to about 1.5.

In some embodiments, the ratio of vinylidene olefin to maleic anhydride is about 0.5 to about 1.0.

In another embodiment, a method of lubricating a machine part may comprise lubricating said machine part with a lubricant composition including the reaction product, or a tribologically acceptable salt or solvate thereof.

In some embodiments, said machine part comprises a gear, an axle, a differential, an engine, a crankshaft, a transmission, or a clutch.

In some embodiments, said transmission is selected from the group consisting of an automatic transmission, a manual transmission, an automated manual transmission, a semi-automatic transmission, a dual clutch transmission, a continuously variable transmission, and a toroidal transmission.

In some embodiments, said clutch comprises a continuously slipping torque converter clutch, a slipping torque converter clutch, a lock-up torque converter clutch, a starting clutch, one or more shifting clutches, or an electronically controlled converter clutch.

In some embodiments, said gear is selected from the group consisting of an automotive gear, a stationary gearbox, and an axle.

In some embodiments, said gear is selected from the group consisting of a hypoid gear, a spur gear, a helical gear, a bevel gear, a worm gear, a rack and pinion gear, a planetary gear set, and an involute gear.

In some embodiments, said differential is selected from the group consisting of a straight differential, a turning differential, a limited slip differential, a clutch-type limited slip differential, and a locking differential.

In some embodiments, said engine is selected from the group consisting of an internal combustion engine, a rotary engine, a gas turbine engine, a four-stroke engine, and a two-stroke engine.

In some embodiments, said engine comprises a piston, a bearing, a crankshaft, and/or a camshaft.

In another embodiment, a method for testing the lubricant properties of a composition using a testing apparatus may comprise lubricating said testing apparatus with a lubricant composition comprising the reaction product described herein, or a tribologically acceptable salt or solvate thereof, said testing apparatus selected from the group consisting of: a Brookfield viscometer, any Vickers Test apparatus, an SAE No. 2 friction test machine, an electric motor-driven Hydra-Matic 4L60-E automatic transmission, ASTM D 471 or D 676 Elastomer Compatibility test equipment, NOACK volatility procedure machine, any test apparatus necessary for ASTM D 2882, D 5182, D 4172, D3233, and D2782 Wear Procedures, ASTM Foaming Procedure apparatus, test apparatus necessary for ASTM D 130 Copper Corrosion test, test equipment specified by the International Harvester Procedure Method BT-9 Rust Control test, test apparatus required by ASTM D 892 Foaming test, test apparatus required by ASTM D 4998 Gear Anti-Wear Performance test, Link M1158 Oil/Friction Machine, L-33-1 Test Apparatus, L-37 Test Apparatus, L-42 Test Apparatus, L-60-1 Test Apparatus, Strama 4-Square Electric Motor-Driven Procedure Machine, FZG Test Apparatus and parts, SSP-180 Procedure Machine, test apparatus for ASTM D 5579 High Temperature Cyclic Durability Procedure, Sauer-Danfoss Series 22 or Series 90 Axial Piston Pump, John Deere Synchro-Plus transmission, an SRV-friction wear tester, a 4-ball test apparatus, an LFW-1 test apparatus, a sprag clutch over-running wear test (SCOWT) apparatus, API CJ-4 engine tests, L-33 Moisture Corrosion Test, High-Temperature Cyclic Durability Test (ASTM D 5579), 288-hour VE engine oil performance test, L-38 standard lubricant test, Denison P46 Piston Pump Test Stand, Sundstrand Dynamic Corrosion Test Stand, a block-on-ring test apparatus, and any test apparatus required for performing test analysis under Mercon®, Mercon® V, Dexron® III, Dexron® III-H, Caterpillar® TO-4, Allison® C-4, JASO, GF-4, GF-5, MIL-E, MIL-L, and Sequences II through VIII.

In another embodiment, a method for improving the low temperature viscometric properties of a lubricating fluid may comprise including in a lubricating fluid an effective amount of one or more reaction products described herein, or a tribologically acceptable salt or solvate thereof.

In another embodiment, a method for improving the low temperature viscometric properties of a lubricating fluid while lubricating an automotive component requiring lubrication, may comprise: 1) adding a lubricating fluid to an automotive component requiring lubrication, said fluid comprising (a) a base oil, and (b) one or more reaction products described herein, or a tribologically acceptable salt or solvate thereof; and 2) operating the automotive component that contains the fluid, wherein the low temperature viscometric performance of the fluid is improved relative to the performance of a lubricating fluid free of the reaction products of 1) (b).

In another embodiment, a method of making a lubricant additive, may comprise: a) reacting a $C_{10}$-$C_{36}$ vinylidene olefin with maleic acid, anhydride, or ester to provide a hydrocarbon-substituted succinic acid, anhydride or ester; and b) aminating the said hydrocarbon-substituted succinic acid, anhydride or ester with an effective amount of a compound containing basic nitrogen.

In another embodiment, a lubricant composition may comprise a mixture of: (a) a major amount of a lubricating oil; and (b) a Brookfield viscosity improving effective amount of a reaction product obtained by: i) reacting a $C_{10}$-$C_{36}$ vinylidene olefin with maleic acid, anhydride, or ester to provide a hydrocarbon-substituted succinic acid, anhydride or ester; and ii) aminating the said hydrocarbon-substituted succinic acid, anhydride or ester with an effective amount of a compound containing basic nitrogen; or a tribologically acceptable salt, solvate, hydrate, or proadditive thereof.

In some embodiments, said $C_{10}$-$C_{36}$ vinylidene olefin represents the formula V:

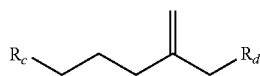

V wherein $R_c$ and $R_d$ are independently a ($C_3$-$C_{15}$) alkyl, cycloalkyl or cycloalkenyl.

In some embodiments, the reaction product is selected from the group consisting of:
(5-methylnonadec-5-en-4-yl)pyrrolidine-2,5-dione;
(6-methylnonadec-6-en-5-yl)pyrrolidine-2,5-dione;
(7-methylnonadec-7-en-6-yl)pyrrolidine-2,5-dione;
(8-methylnonadec-8-en-7-yl)pyrrolidine-2,5-dione;
(9-methylnonadec-9-en-8-yl)pyrrolidine-2,5-dione;
(10-methylnonadec-10-en-9-yl)pyrrolidine-2,5-dione;
(9-methylnonadec-8-en-10-yl)pyrrolidine-2,5-dione;
(8-methylnonadec-7-en-9-yl)pyrrolidine-2,5-dione;
(7-methylnonadec-6-en-8-yl)pyrrolidine-2,5-dione;
(6-methylnonadec-5-en-7-yl)pyrrolidine-2,5-dione;
(5-methylnonadec-4-en-6-yl)pyrrolidine-2,5-dione;
(4-methylnonadec-3-en-5-yl)pyrrolidine-2,5-dione;
(3-methylnonadec-2-en-4-yl)pyrrolidine-2,5-dione;
(2,2'-(ethane-1,2-diylbis(azanediyl))bis(ethane-2,1-diyl))bis
(3-(8-methylnonadec-8-en-7-yl)pyrrolidine-2,5-dione);
(3-methylhenicos-2-en-4-yl)pyrrolidine-2,5-dione;
(4-methylhenicos-3-en-5-yl)pyrrolidine-2,5-dione;
(5-methylhenicos-4-en-6-yl)pyrrolidine-2,5-dione;
(6-methylhenicos-5-en-7-yl)pyrrolidine-2,5-dione;
(7-methylhenicos-6-en-8-yl)pyrrolidine-2,5-dione;
(8-methylhenicos-7-en-9-yl)pyrrolidine-2,5-dione;
(9-methylhenicos-8-en-10-yl)pyrrolidine-2,5-dione;
(10-methylhenicos-9-en-11-yl)pyrrolidine-2,5-dione;
(11-methylhenicos-11-en-10-yl)pyrrolidine-2,5-dione;
(10-methylhenicos-10-en-9-yl)pyrrolidine-2,5-dione;
(9-methylhenicos-9-en-8-yl)pyrrolidine-2,5-dione;
(8-methylhenicos-8-en-7-yl)pyrrolidine-2,5-dione;
(7-methylhenicos-7-en-6-yl)pyrrolidine-2,5-dione;
(6-methylhenicos-6-en-5-yl)pyrrolidine-2,5-dione;
(5-methylhenicos-5-en-4-yl)pyrrolidine-2,5-dione;
(2,2'-(ethane-1,2-diylbis(azanediyl))bis(ethane-2,1-diyl))bis
(3-(5-methylhenicos-5-en-4-yl)pyrrolidine-2,5-dione);
(5-methyltricos-5-en-4-yl)pyrrolidine-2,5-dione;
(6-methyltricos-6-en-5-yl)pyrrolidine-2,5-dione;
(7-methyltricos-7-en-6-yl)pyrrolidine-2,5-dione;
(8-methyltricos-8-en-7-yl)pyrrolidine-2,5-dione;
(9-methyltricos-9-en-8-yl)pyrrolidine-2,5-dione;
(10-methyltricos-10-en-9-yl)pyrrolidine-2,5-dione;
(11-methyltricos-11-en-10-yl)pyrrolidine-2,5-dione;
(12-methyltricos-12-en-11-yl)pyrrolidine-2,5-dione;
(11-methyltricos-10-en-12-yl)pyrrolidine-2,5-dione;
(10-methyltricos-9-en-11-yl)pyrrolidine-2,5-dione;
(9-methyltricos-8-en-10-yl)pyrrolidine-2,5-dione;
(8-methyltricos-7-en-9-yl)pyrrolidine-2,5-dione;
(7-methyltricos-6-en-8-yl)pyrrolidine-2,5-dione;
(6-methyltricos-5-en-7-yl)pyrrolidine-2,5-dione;
(5-methyltricos-4-en-6-yl)pyrrolidine-2,5-dione;
(4-methyltricos-3-en-5-yl)pyrrolidine-2,5-dione;
(3-methyltricos-2-en-4-yl)pyrrolidine-2,5-dione;
(2,2'-ethane-1,2-diylbis(azanediyl))bis(ethane-2,1-diyl))bis
(3-(5-methyltricos-5-en-4-yl)pyrrolidine-2,5-dione);
(3-methylpentacos-2-en-4-yl)pyrrolidine-2,5-dione;
(4-methyl pentacos-3-en-5-yl)pyrrolidine-2,5-dione;
(5-methylpentacos-4-en-6-yl)pyrrolidine-2,5-dione;
(6-methylpentacos-5-en-7-yl)pyrrolidine-2,5-dione;
(7-methylpentacos-6-en-8-yl)pyrrolidine-2,5-dione;
(8-methyl pentacos-7-en-9-yl)pyrrolidine-2,5-dione;
(9-methylpentacos-8-en-10-yl)pyrrolidine-2,5-dione;
(10-methyl pentacos-9-en-11-yl)pyrrolidine-2,5-dione;
(11-methyl pentacos-10-en-12-yl)pyrrolidine-2,5-dione;
(12-methylpentacos-11-en-13-yl)pyrrolidine-2,5-dione;
(13-methylpentacos-13-en-12-yl)pyrrolidine-2,5-dione;
(12-methyl pentacos-12-en-11-yl)pyrrolidine-2,5-dione;
(11-methylpentacos-11-en-10-yl)pyrrolidine-2,5-dione;
(10-methylpentacos-10-en-9-yl)pyrrolidine-2,5-dione;
(9-methylpentacos-9-en-8-yl)pyrrolidine-2,5-dione;
(8-methylpentacos-8-en-7-yl)pyrrolidine-2,5-dione;
(7-methylpentacos-7-en-6-yl)pyrrolidine-2,5-dione;
(6-methylpentacos-6-en-5-yl)pyrrolidine-2,5-dione;
(5-methylpentacos-5-en-4-yl)pyrrolidine-2,5-dione;
(2,2'-(ethane-1,2-diylbis(azanediyl))bis(ethane-2,1-diyl))bis
(3-(7-methylpentacos-7-en-6-yl)pyrrolidine-2,5-dione);
and a tribologically acceptable salt or solvate thereof.

In some embodiments, the Brookfield improving effective amount comprises a BV −40 of less than about 10,000 cP based on the lubricant composition.

A further aspect of the present disclosure may be directed toward a transmission lubricated with a lubricant composition comprising a compound of formula I. Exemplary transmissions may include those described in "Transmission and Driveline Design", SAE Paper Number SP-108, Society of Automotive Engineers, Warrendale Pa. 1995; "Design of Practices: Passenger Car Automotive Transmissions", The Third Edition, SAE Publication #AE-18, Society of Automotive Engineers, Warrendale Pa. 1994; and "Automotive Transmission Advancements", SAE Paper Number SP-854, Society of Automotive Engineers, Warrendale Pa. 1991.

The present disclosure may also include isotopically-labeled compounds, which are identical to those recited in formula I, but for the fact that one or more atoms are replaced by an atom having an atomic mass or mass number different from the atomic mass or mass number usually found in nature. Examples of isotopes that can be incorporated into compounds of the present disclosure include isotopes of hydrogen, carbon, nitrogen, oxygen, phosphorous, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Compounds of the present disclosure, proadditives thereof, and tribologically acceptable salts of said compounds or of said proadditives which contain the aforementioned isotopes and/or other isotopes of other atoms are within the scope of the present disclosure. Phosphorus-31, i.e., $^{31}$P, and carbon-13, i.e., $^{13}$C, isotopes are particularly preferred for their ease of preparation and detectability. Isotopically-labeled compounds of formula I of the present disclosure and proadditives thereof can generally be prepared by carrying out the procedures disclosed by substituting a readily available isotopically-labeled reagent for a non-isotopically-labeled reagent.

The present disclosure also relates to the tribologically acceptable acid addition salts of compounds of the formula I. The acids which are used to prepare the tribologically acceptable acid addition salts of the aforementioned base compounds of the present disclosure are those which form acid addition salts, i.e., salts containing tribologically acceptable anions, such as the chloride, bromide, iodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)]salts.

The present disclosure also relates to base addition salts of formula I. The chemical bases that may be used as reagents to prepare tribologically acceptable base salts of those compounds of formula I that are acidic in nature are those that form base salts with such compounds. Such base salts include, but are not limited to cations such as alkali metal cations (e.g., potassium and sodium) and alkaline earth metal cations (e.g., calcium and magnesium), ammonium or amine addition salts such as N-methylglucamine-(meglumine), and alkanolammonium and other base salts of tribologically acceptable organic amines.

The phrase "tribologically acceptable salt(s)", as used herein, unless otherwise indicated, includes salts of acidic or basic groups which may be present in the compounds of the present disclosure. The compounds of the present disclosure that are basic in nature are capable of forming a wide variety of salts with various inorganic and organic acids. The acids that may be used to prepare tribologically acceptable acid addition salts of such basic compounds are those that form acid addition salts, i.e., salts containing tribologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts. The compounds of the present disclosure that include a basic moiety, such as an amino group, may form tribologically acceptable salts with various amines, in addition to the acids mentioned above.

The present disclosure also encompasses lubricant or tribological compositions containing proadditives of compounds of the formula I. Compounds of formula I having free amino, amido, hydroxy or carboxylic groups can be converted into proadditives. Proadditives include compounds wherein an amino residue, carbonates, carbamates, amides, alkyl esters, etc. are covalently bonded to the substituents of formula I but are sufficiently labile under typical lubricant use conditions that the proadditive yields a compound of formula I.

The present disclosure also encompasses compounds of formula I containing protective groups. One skilled in the art will also appreciate that compounds of the present disclosure can also be prepared with certain protecting groups that are useful for purification or storage and can be removed before use in the device to be lubricated. The protection and deprotection of functional groups is described in "Protective Groups in Organic Chemistry", edited by J. W. F. McOmie, Plenum Press (1973) and "Protective Groups in Organic Synthesis", 3rd edition, T. W. Greene and P. G. M. Wuts, Wiley-Interscience (1999).

The compounds of the present disclosure include all stereoisomers (e.g., cis and trans isomers) and all optical isomers of compounds of the formula I (e.g., R and S enantiomers), as well as racemic, diastereomeric and other mixtures of such isomers.

The compounds, salts and proadditives of the present disclosure can exist in several tautomeric forms, including the enol and imine form, and the keto and enamine form and geometric isomers and mixtures thereof. All such tautomeric forms are included within the scope of the present disclosure. Even though one tautomer may be described, the present disclosure includes all tautomers of the present compounds.

The present disclosure also includes atropisomers of the present disclosure. Atropisomers refer to compounds of formula I that can be separated into rotationally restricted isomers.

The compounds of the present disclosure may contain olefin-like double bonds. When such bonds are present, the compounds of the present disclosure exist as cis and trans configurations and as mixtures thereof.

As used herein, the notation

refers to a point of attachment. Thus the structure:

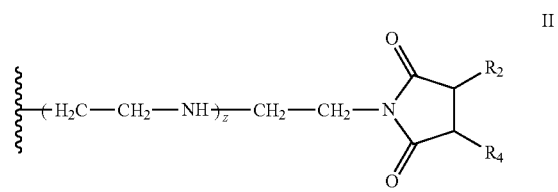

indicates that the point of attachment is the carbon atom of the N$_2$C— group.

The term "interrupted by" refers to compounds in which a ring carbon atom is replaced by an element selected from the group consisting of (C═O), —SO$_2$—, —S—, —O—, —P—, —N—, —NH—, and —NR$^{12}$. For example, if a substituent is —(C$_6$-C$_{10}$)aryl, such as

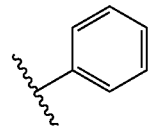 [SMILES: *c1ccccc1]

the ring may be interrupted or replaced by a nitrogen heteroatom to form the following ring:

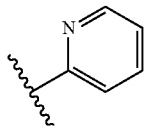

such that a ring carbon is replaced by the heteroatom nitrogen. Compounds of the present disclosure can accommodate up to three such replacements or interruptions.

A "suitable substituent" is intended to mean a chemically and tribologically acceptable functional group i.e., a moiety that does not negate the tribological activity of the inventive compounds. Such suitable substituents may be routinely selected by those skilled in the art. Illustrative examples of suitable substituents include, but are not limited to halo groups, perfluoroalkyl groups, perfluoroalkoxy groups, alkyl groups, alkenyl groups, alkynyl groups, hydroxy groups, oxo groups, mercapto groups, alkylthio groups, alkoxy groups, aryl or heteroaryl groups, aryloxy or heteroaryloxy groups, aralkyl or heteroaralkyl groups, aralkoxy or heteroaralkoxy groups, HO—(C=O)— groups, amino groups, alkyl- and dialkylamino groups, carbamoyl groups, alkylcarbonyl groups, alkoxycarbonyl groups, alkylaminocarbonyl groups dialkylamino carbonyl groups, arylcarbonyl groups, aryloxycarbonyl groups, alkylsulfonyl groups, arylsulfonyl groups and the like. Those skilled in the art will appreciate that many substituents can be substituted by additional substituents. Further examples of suitable substituents include those recited in the definition of compounds of formula I, including $R_1$ through $R_{15}$, as defined herein.

As used herein, the term "alkyl," as well as the alkyl moieties of other groups referred herein (e.g., alkoxy), may be linear or branched (such as methyl, ethyl, n-propyl, isopropyl, n-butyl, iso-butyl, secondary-butyl, tertiary-butyl); optionally substituted by 1 to 3 suitable substituents as defined above such as fluoro, chloro, trifluoromethyl, $(C_1-C_6)$alkoxy, $(C_6-C_{10})$aryloxy, trifluoromethoxy, difluoromethoxy or $(C_1-C_6)$alkyl. The phrase "each of said alkyl" as used herein refers to any of the preceding alkyl moieties within a group such as alkoxy, alkenyl or alkylamino. Preferred alkyls include $(C_1-C_{22})$alkyl, more preferred are $(C_1-C_6)$alkyl, and most preferred are methyl and ethyl.

As used herein, the term "cycloalkyl" refers to a mono, bicyclic or tricyclic carbocyclic ring (e.g., cyclopropyl, cyclobutyl, cyclopentyl, cyclohexyl, cycloheptyl, cyclooctyl, cyclononyl, cyclopentenyl, cyclohexenyl, bicycloheptanyl, bicyclooctanyl and bicyclononanyl, etc.); optionally containing 1 or 2 double bonds and optionally substituted by 1 to 3 suitable substituents as defined above which includes but is not limited to fluoro, chloro, trifluoromethyl, $(C_1-C_6)$alkoxy, $(C_6-C_{10})$aryloxy, trifluoromethoxy, difluoromethoxy or $(C_1-C_6)$alkyl.

As used herein, the term "halogen" includes fluoro, chloro, bromo or iodo or fluoride, chloride, bromide or iodide.

As used herein, the term "alkenyl" means straight or branched chain unsaturated radicals of 2 to 22 carbon atoms, including, but not limited to ethenyl, 1-propenyl, 2-propenyl (allyl), iso-propenyl, 2-methyl-1-propenyl, 1-butenyl, 2-butenyl, and the like; optionally substituted by 1 to 3 suitable substituents as defined above which includes but is not limited to fluoro, chloro, trifluoromethyl, $(C_1-C_6)$alkoxy, $(C_6-C_{10})$aryloxy, trifluoromethoxy, difluoromethoxy or $(C_1-C_6)$alkyl.

As used herein, the term "alkynyl" is used herein to mean straight or branched hydrocarbon chain radicals having one triple bond including, but not limited to, ethynyl, propynyl, butynyl, and the like; optionally substituted by 1 to 3 suitable substituents as defined above which includes but is not limited to fluoro, chloro, trifluoromethyl, $(C_1-C_6)$alkoxy, $(C_6-C_{10})$aryloxy, trifluoromethoxy, difluoromethoxy or $(C_1-C_6)$alkyl.

As used herein, the term "carbonyl" or "(C=O)" (as used in phrases such as alkylcarbonyl, alkyl-(C=O)— or alkoxycarbonyl) refers to the joinder of the >C=O moiety to a second moiety such as an alkyl or amino group (i.e. an amido group). Alkoxycarbonylamino (i.e. alkoxy(C=O)—NH—) refers to an alkyl carbamate group. The carbonyl group is also equivalently defined herein as (C=O). Alkylcarbonylamino refers to groups such as acetamide.

As used herein, the term "aryl" means aromatic radicals which includes but is not limited to phenyl, naphthyl, tetrahydronaphthyl, indanyl and the like; optionally substituted by 1 to 3 suitable substituents as defined above.

As used herein, the term "heteroaryl" refers to an aromatic heterocyclic group usually with one heteroatom selected from O, S and N in the ring. In addition to said heteroatom, the aromatic group may optionally have up to four N atoms in the ring. For example, heteroaryl group includes pyridyl, pyrazinyl, pyrimidinyl, pyridazinyl, thienyl, furyl, imidazolyl, pyrrolyl, oxazolyl (e.g., 1,3-oxazolyl, 1,2-oxazolyl), thiazolyl (e.g., 1,2-thiazolyl, 1,3-thiazolyl), pyrazolyl, tetrazolyl, triazolyl (e.g., 1,2,3-triazolyl, 1,2,4-triazolyl), oxadiazolyl (e.g., 1,2,3-oxadiazolyl), thiadiazolyl (e.g., 1,3,4-thiadiazolyl), quinolyl, isoquinolyl, benzothienyl, benzofuryl, indolyl, and the like; optionally substituted by 1 to 3 suitable substituents as defined above which includes but is not limited to fluoro, chloro, trifluoromethyl, $(C_1-C_6)$alkoxy, $(C_6-C_{10})$aryloxy, trifluoromethoxy, difluoromethoxy or $(C_1-C_6)$alkyl.

The term "heterocyclic" as used herein refers to a cyclic group containing 1-9 carbon atoms and 1 to 4 hetero atoms selected from N, P, O, $S(O)_n$ or NR. Examples of such rings include dioxaphosphorinane, azetidinyl, tetrahydrofuranyl, imidazolidinyl, pyrrolidinyl, piperidinyl, piperazinyl, oxazolidinyl, thiazolidinyl, pyrazolidinyl, thiomorpholinyl, tetrahydrothiazinyl, tetrahydrothiadiazinyl, morpholinyl, oxetanyl, tetrahydrodiazinyl, oxazinyl, oxathiazinyl, indolinyl, isoindolinyl, quinuclidinyl, chromanyl, isochromanyl, benzoxazinyl, and the like. Examples of said monocyclic saturated or partially saturated ring systems are 1,3,2-dioxaphosphorinane, tetrahydrofuran-2-yl, tetrahydrofuran-3-yl, imidazolidin-1-yl, imidazolidin-2-yl, imidazolidin-4-yl, pyrrolidin-1-yl, pyrrolidin-2-yl, pyrrolidin-3-yl, piperidin-1-yl, piperidin-2-yl, piperidin-3-yl, piperazin-1-yl, piperazin-2-yl, piperazin-3-yl, 1,3-oxazolidin-3-yl, isothiazolidine, 1,3-thiazolidin-3-yl, 1,2-pyrazolidin-2-yl, 1,3-pyrazolidin-1-yl, thiomorpholin-yl, 1,2-tetrahydrothiazin-2-yl, 1,3-tetrahydrothiazin-3-yl, tetrahydrothiadiazin-yl, morpholin-yl, 1,2-tetrahydrodiazin-2-yl, 1,3-tetrahydrodiazin-1-yl, 1,4-oxazin- 2-yl, 1,2,5-oxathiazin-4-yl and the like; optionally containing 1 or 2 double bonds and optionally substituted by 1 to 3 suitable substituents as defined above which includes but is not limited to fluoro, chloro, trifluoromethyl, $(C_1\text{-}C_6)$alkoxy, $(C_6\text{-}C_{10})$aryloxy, trifluoromethoxy, difluoromethoxy or $(C_1\text{-}C_6)$alkyl.

Nitrogen heteroatoms as used herein refers to N=, >N and —NH; wherein —N= refers to a nitrogen double bond; >N refers to a nitrogen containing two bond connections and —N refers to a nitrogen containing one bond.

"Embodiment" as used herein refers to specific groupings of compounds or uses into discrete subgenera. Such subgenera may be cognizable according to one particular substituent such as a specific $R_1$ or $R_4$ group. Other subgenera are cognizable according to combinations of various substituents, such as all compounds wherein $R_2$ is hydrogen and $R_1$ is $(C_1\text{-}C_6)$alkyl.

As used herein, the terms "oil composition," "lubrication composition," "lubricating oil composition," "lubricating oil," "lubricant composition," "fully formulated lubricant composition," and "lubricant" are considered synonymous, fully interchangeable terminology referring to the finished lubrication product comprising a major amount of a base oil plus a minor amount of an additive composition.

As used herein, the terms "additive package," "additive concentrate," and "additive composition" are considered synonymous, fully interchangeable terminology referring the portion of the lubricating composition excluding the major amount of base oil stock mixture.

As used throughout the specification and claims, "a" and/or an may refer to one or more than one. Unless otherwise indicated, all numbers expressing quantities of ingredients, properties such as molecular weight, percent, ratio, reaction conditions, and so forth used in the specification and claims are to be understood as being modified in all instances by the term "about." Accordingly, unless indicated to the contrary, the numerical parameters set forth in the specification and claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

Additional objects and advantages of the disclosure will be set forth in part in the description which follows, and/or may be learned by practice of the disclosure. The objects and advantages of the disclosure will be realized and attained by means of the elements and combinations particularly pointed out in the appended claims.

It is to be understood that both the foregoing general description and the following detailed description are exemplary and explanatory only and are not restrictive of the disclosure, as claimed.

DETAILED DESCRIPTION

The compounds of formulas 1 and 1(a) can be prepared using the synthetic route outlined in Scheme I. The substituents in Scheme I have the same meaning as the substituents defined for formula I.

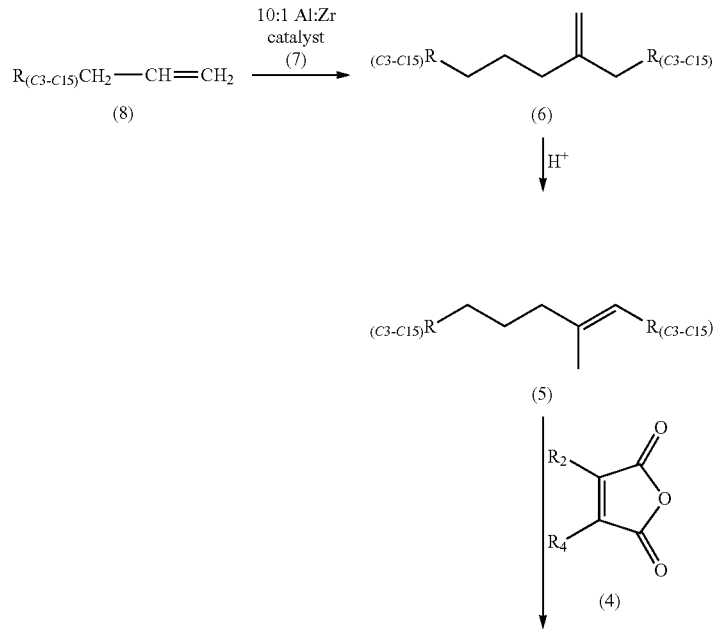

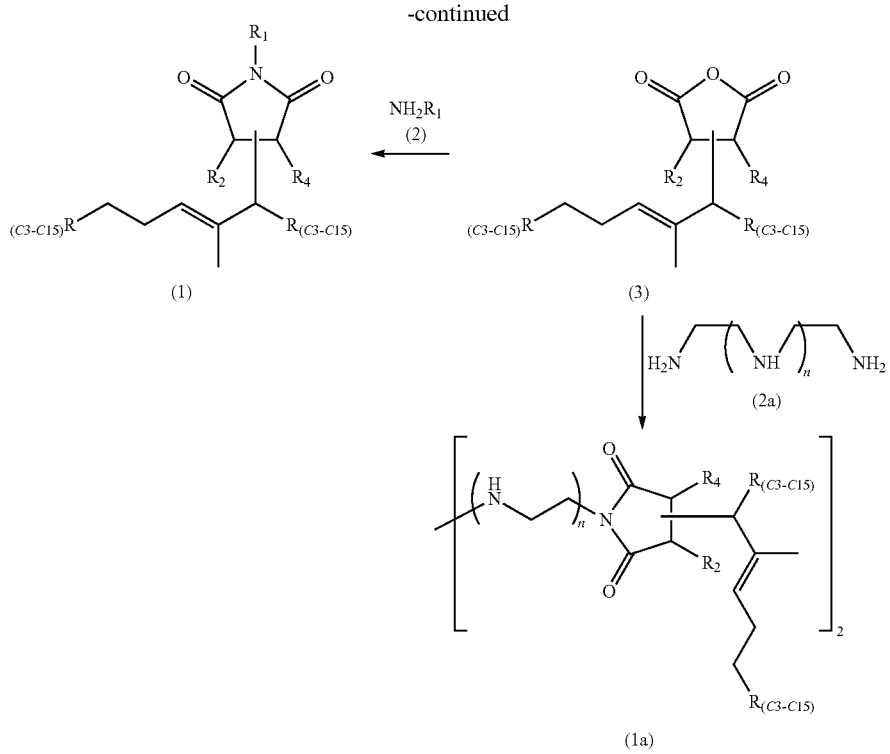

Compounds of formula (1) and (1a) can be prepared by dimerizing an alpha-olefin of the general formula $RCH_2CH{=}CH_2$ (8), where R is alkyl, cycloalkyl, or cycloalkenyl with a carbon number ranging from $C_3$-$C_{15}$, to a vinylidene olefin (6) by contacting the olefin with a metallic catalyst system such as, e.g., a zirconium metallocene and alkylaluminoxane catalyst system (7). Dimerization yields can be expected at as high as ninety (90) percent. This method is well-known and discussed in the patent literature (see, e.g., U.S. Pat. No. 5,087,788).

The vinylidene (6) may be converted to a more thermodynamically stable tri-substituted internal olefin (5) by placing the vinylidene under acid-catalysis conditions. The resulting olefin is treated with a maleic acid, anhydride, or ester (a maleic anhydride (4) is shown in Scheme I), optionally substituted at the $R_2$ and $R_4$ positions, under thermal conditions to induce an "ene reaction." The reaction product (3), an alkyl succinic anhydride having a vinyl methyl group, is freed from unreacted maleic anhydride by placing the reaction mixture under vacuum. An amination reaction may then be conducted at a suitable temperature conducive to promoting the reaction. The reaction mixture may be neutralized with an equivalent amount of base, e.g., ammonia gas or a substituted amine (2) at a suitable elevated temperature. The final product (1), an alkyl succinimide having a vinyl methyl group, is produced with overall yields at or above eighty (80) percent. Alternatively, the alkyl succinic anhydride (3) can be reacted with a polyamine type (2a) to provide a bis-succinimide (1a) with both succinimides substituted by alkyl groups containing a vinyl methyl group.

In some embodiments, one or more compounds according to formula I, or a tribologically acceptable salt or solvate thereof may be incorporated into a lubricating composition. A lubricant additive composition may be prepared comprising one or more compounds according to formula I, or a tribologically acceptable salt or solvate thereof. A lubricant composition may comprise a) a major amount of a base oil; and b) a minor amount of an additive composition comprising one or more compounds of formula I, or a tribologically acceptable salt or solvate thereof.

Optional Additive Components

In another aspect of the present disclosure, the alkyl succinimides with vinyl methyl substitution may be formulated into an additive composition and blended with a base oil to obtain a lubricating fluid. Such a fluid may be formulated optionally with one or more selected ingredients and additives that include, without limitation, those described hereinbelow. Such additives may include, but are not limited to, air expulsion additives, antifoamants (foam inhibitors), antioxidants, anti-rust additives, antiwear additives, colorants, corrosion inhibitors, dispersants, extreme pressure agents, friction modifiers, metal deactivators, metallic detergents, organic phosphorus compounds, pour point depressants, seal swell agents, and/or viscosity index improvers. Additives are generally described in C. V. Smalheer et al., Lubricant Additives, pages 1-11 (1967) and in U.S. Pat. No. 4,105,571, among others. The supplemental additives include those that are commercially available.

Suitable oil-soluble ashless dispersants may be selected from the group consisting of: a succinimide dispersant, a succinic ester dispersant, a succininic ester-amide dispersant, a Mannich base dispersant, phosphorylated forms thereof, and boronated forms thereof.

In selecting any of the optional additives, it may be important to ensure that the selected component(s) may be soluble or stably dispersible in the additive package and the finished lubricant composition, and may be compatible with the other components of the composition. By preference, a person skilled in the art may be expected to choose an additional optional additive or combination of additives, amounts thereof, such that the performance properties of the composition, such as the improved low temperature viscometrics, among other properties, needed or desired, as applicable, in the overall finished composition, may not be substantially adversely affected.

In general, the ancillary additive components may be employed in the lubricating oil in minor amounts sufficient to improve the performance characteristics and properties of the base fluid. The amounts may thus vary in accordance with such factors as the viscosity characteristics of the base fluid employed, the viscosity characteristics desired in the finished fluid, the service conditions for which the finished fluid is intended, and the performance characteristics desired in the finished fluid.

However, generally speaking, the following general concentrations (weight percent unless otherwise indicated) of the additional components in the base fluids may be illustrative.

Respective amounts of additives may be blended into a selected base oil in amounts that may be sufficient to provide their expected performance. An effective amount for a specific formulation may be readily ascertained, but for illustrative purposes these general guides for representative effective amounts are provided. The amounts below are given in weight % of the fully formulated lubricating fluid.

| Component | Example Ranges 1 and 2 | |
|---|---|---|
| Dispersants | 0-20 | 2-8 |
| Friction Modifier(s) | 0-10 | 0.05-5 |
| Detergents | 0-5 | 0.01-1 |
| Viscosity Index Improver | 0-30 | 5-15 |
| Antioxidants | 0-2 | 0.1-1 |
| Rust inhibitor | 0-1 | 0.05-0.5 |
| Corrosion Inhibitor | 0-5 | 0.05-2 |
| Antiwear agent | 0-5 | 0.25-2 |
| Seal Swell Agent | 0-10 | 0.5-5 |
| Antifoam Agent | 0-0.5 | 0.001-0.1 |
| Lubricating Base Oil | Balance | |

It will be appreciated that the individual components employed may be separately blended into the base fluid or may be blended therein in various sub-combinations, if desired. Ordinarily, the particular sequence of such blending steps is not crucial. Moreover, such components may be blended in the form of separate solutions in a diluent. It may be preferable, however, to blend the additive components used in the form of a concentrate, as this simplifies the blending operations, reduces the likelihood of blending errors, and takes advantage of the compatibility and solubility characteristics afforded by the overall concentrate.

Additive concentrates may thus be formulated to contain all of the additive components and if desired, some of the base oil component, in amounts proportioned to yield finished fluid blends consistent with the concentrations described above. In most cases, the additive concentrate will contain one or more diluents such as light mineral oils, to facilitate handling and blending of the concentrate. Thus concentrates containing up to about 50 wt. % of one or more diluents or solvents may be used, provided the solvents are not present in amounts that interfere with the low and high temperature and flash point characteristics and the performance of the finished power transmission fluid composition. In this regard, the additive components used pursuant to this disclosure may be selected and proportioned such that an additive concentrate or package formulated from such components will have a flash point of about 170° C. or above, using the ASTM D-92 test procedure.

Lubricating fluids of the embodiments herein may be formulated to provide lubrication and/or enhanced friction performance properties and/or improved low temperature viscometric properties for various applications. A lubricant composition including a compound of formula I, or a tribologically acceptable salt or solvate thereof, may be used for lubricating a machine part.

Such fluids may be suitable for automatic or manual transmissions, including step automatic transmissions, continuously variable transmissions, semi-automatic transmissions, automated manual transmissions, toroidal transmissions, and dual clutch transmissions. Such transmissions include four-, five-, six-, and seven-speed transmissions, and continuously variable transmissions (chain, belt, or disk type). Further, the lubricating fluids of the present disclosure also are suitable for use in transmissions with an electronically controlled converter clutch, a slipping torque converter, a continuously slipping torque converter clutch, a lock-up torque converter, a starting clutch, and/or one or more shifting clutches. Lubricating fluids according to the present disclosure may also be used in gear applications, such as industrial gear applications, automotive gear applications, axles, and stationary gearboxes. Gear-types may include, but are not limited to, spur, spiral, worm, rack and pinion, involute, bevel, helical, planetary, and hypoid gears. The presently disclosed lubricating fluids may be used in axles, transfer cases, differentials, such as straight differentials, turning differentials, limited slip differentials, clutch-type differentials, and locking differentials, and the like. Lubricating fluids of the present disclosure may be used in various engine applications, including but not limited to, internal combustion engines, rotary engines, gas turbine engines, four-stroke engines, and two-stroke engines. Engine components that may be lubricated with presently disclosed additives may include pistons, bearings, crankshafts, and/or camshafts. Further, they may also be useful in metalworking applications. A further aspect of the present disclosure may provide lubricant composition comprising a lubricant additive as described herein, wherein the lubricant composition is suitable for lubricating moving components or parts of a truck, an automobile, and/or a piece of mechanized farm equipment, such as a tractor or reaper.

EXAMPLES

Example 1

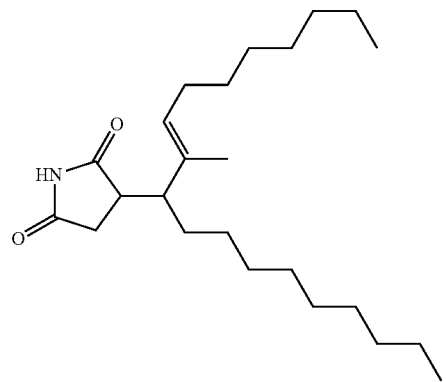 [SMILES: CCCCCCC/C=C(\C)C(CCCCCCCCC)C1CC(=O)NC1=O]

339.4 grams of $C_{20}$-$C_{24}$ olefin (1.1 mol), containing approximately forty (40) wt. % internal vinylidene, 112.8 grams (1.2 mol) of molten maleic anhydride, 2.42 grams p-toluenesulfonic acid (TsOH), and 1.64 grams of synthetic antioxidant (a hindered phenol antioxidant) were charged into a 1.0 L autoclave. The stirred mixture was subjected to vacuum (28 inches of Hg), nitrogen flush, and vacuum cycle as it was heated with stirring. After about 5 hours at a temperature of about 225° C. the resulting alkyl succinic anhydride was transferred to a separate reactor where unreacted maleic anhydride was removed by distillation. Ammonia gas linear $C_{20}$ succinimide structure includes (E)-3-(icos-8-en-8-yl)pyrrolidine-2,5-dione, shown above.

Example 3

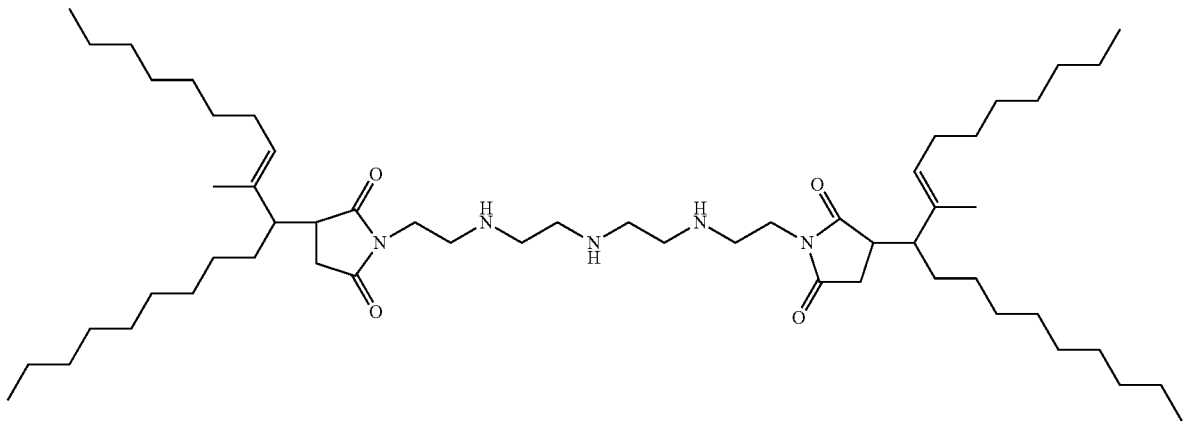

(16.95 grams) was bubbled into the stirred mixture at about 160° C. over the course of from about 2 to about 3 hours. The hot mixture was vacuum filtered to provide a clear product containing 2.29% N. Infrared spectrum of the clear product showed carbonyl bands at 1771, 1709 cm$^{-1}$ (imide). The amount of acidic groups titratible with a strong base was 2.07 milliequivalents per gram of sample. A representative vinylidene $C_{20}$ succinimide structure includes (9-methylnonadec-8-en-10-yl)pyrrolidine-2,5-dione, shown above.

Example 2

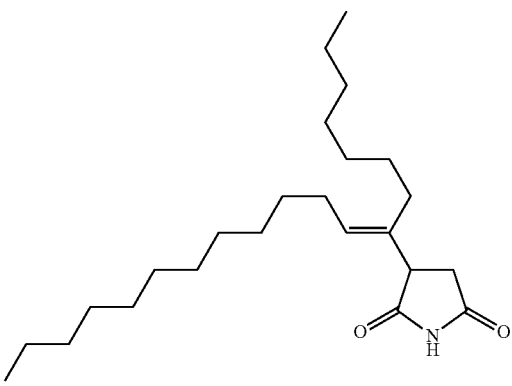 [SMILES: CCCCCCCCCCC/C=C(\CCCCCCC)C1CC(=O)NC1=O]

450.0 grams of linear alpha $C_{20}$-$C_{24}$ olefin (1.5 mol), 149.6 grams (1.5 mol) of molten maleic anhydride, 3.21 grams p-toluenesulfonic acid (TsOH), and 2.20 grams of synthetic antioxidant (a hindered phenol antioxidant) were charged into a 2.0 L autoclave. The stirred mixture, which was sealed under vacuum, was stirred and heated for about 5 hours at 225° C. The resulting alkyl succinic anhydride was transferred to a separate reactor where unreacted maleic anhydride was removed by distillation. A portion of this intermediate product (99.0 grams) was neutralized with ammonia gas (4.21 grams) at 160° C. to produce 98.8 grams of the succinimide that contained 2.94% N. A representative isomerized 344.9 grams of $C_{20}$-$C_{24}$ olefin (1.1 mol), containing approximately forty (40) wt. % internal vinylidene, 114.6 grams (1.2 mol) of molten maleic anhydride, 2.46 grams p-toluenesulfonic acid (TsOH), and 1.67 grams of synthetic antioxidant (a hindered phenol antioxidant) were charged into a 1.0 L autoclave. The stirred mixture was subjected to vacuum (28 inches of Hg), nitrogen flush, and vacuum cycle as it was heated with stirring. After about 5 hours at about 225° C., the resulting alkyl succinic anhydride was transferred to a separate reactor where unreacted maleic anhydride was removed by distillation. The product was diluted with 45.0 g of process oil. Drop-wise addition of 43.9 grams of commercial tetraethylenepentamine (TEPA) under temperature controlled conditions produced a mixture that was stirred at 160° C., under vacuum for 3 hours. The product (258.5 g) contained 6.09% N and had a total base number (TBN) of 146.5 mg KOH/g. A representative vinylidene $C_{20}$ bis-succinimide structure includes (2,2'-(2,2'-azanediylbis(ethane-2,1-diyl)bis(azanediyl))bis(ethane-2,1-diyl))bis(3-((E)-9-methylnonadec-8-en-10-yl)pyrrolidine-2,5-dione), shown above.

The lubricant additives of the present disclosure according to Examples 1 and 3 and a comparison friction modifier, Example 2, were formulated into power transmitting fluids designated Samples S1, S2, and S3, wherein S1 and S3 contained lubricant additives according to Examples 1 and 3 respectively. And S2 contained a lubricant additive according to Example 2. The power transmitting fluids were otherwise identical except for the friction modifier. The power transmitting fluids each contain about 3.5 wt. % of a respective friction modifier. Typical power transmitting fluids utilizing the friction modifiers of the present invention contain between about 1 and 10 wt. % of the inventive friction modifier(s).

The Brookfield Viscosity at −40° C. (BV −40) for each power transmitting fluid containing components according to Examples 1-3 was ascertained and reported in Table 1.

TABLE 1

Comparison of Brookfield Viscosity and Friction Data

| Samples | FM from Example # | BV −40° C. (cP) | $\mu_{avg}$ (1-50 rpm) | SAE #2 Machine Friction Data $d\mu/dv$ (1-50 rpm)*100 | $d\mu/dv$ (100-300 rpm)*100 |
|---|---|---|---|---|---|
| S1 | 1 | 5720 | 0.133 | 5.26 | −0.21 |
| S2 | 2 | 31,600 | 0.126 | 6.14 | −0.14 |
| S3 | 3 | 6020 | 0.140 | 8.77 | 0.29 |

Brookfield viscosity results for the lubricating fluids that contain the additives described in Examples 1, 2 and 3 are shown in Table 1 as entries S1, S2, and S3, respectively. The striking feature of the data is the extent of Brookfield viscosity improvement resulting from the use of the internal vinylidene-derived succinimide product (S1) in comparison to the one prepared from a linear alpha olefin (S2). This difference may translate to a significant cost saving due to elimination of the need for expensive synthetic fluids and/or viscosity index improvers (VIIs). The bis-succinimide-type product (S3) that contains methyl branched hydrocarbon chains represented by the present disclosure also shows a favorable Brookfield viscosity. Table 1 displays another distinct feature of the bis-succinimide-type product (S3) that relates to the bis-succinimide frictional characteristics.

Friction performance of lubricating fluids that contain Samples S1, S2, and S3 were evaluated in a SAE No. 2 machine that allows precise measurement of the coefficient of friction at different sliding speeds ($\mu/v$). A conventional SAE No. 2 machine is equipped with a motor having a shaft extending at both ends. The inertia end is flanged to a flywheel. The clutch end carries the test head where friction force between friction plates and steel separator plates is measured through a load cell at a given temperature, load, and sliding speed.

The $\mu/v$ data obtained with the machine provides a good correlation of vehicle shudder and fuel efficiency performance. Power transmission fluids showing a more negative gradient in the $\mu/v$ data indicate tendencies toward more severe shudder in the vehicle. As will be appreciated by those skilled in the art, friction at low speed (low rpm's, e.g., low velocity V) in a range of about 1 to about 50 rpm, for instance, is indicative of torque capacity, that is, the ability to transmit energy. A higher value indicates less energy loss by the transmission which translates to better fuel efficiency. Thus, the most preferred fluid will be one that shows high friction without exhibiting negative slope in the $\mu/v$ curve.

Close inspection of Table 1, reveals a comparable tendency to shudder for lubricating fluids of samples S1 and S2. However, the lubricating fluid of the present disclosure (sample S1) provides better torque capacity. When combined with the Brookfield viscosity benefit discussed above, lubricating fluid of the present disclosure (S1) represents a better lubricating fluid than that of sample S2 that is made from linear alpha olefin. The bis-succinimide type friction modifier (S3) made from the vinylidene containing olefin exhibits the least tendency to shudder by maintaining a positive slope throughout the $\mu/v$ curve. The bis-succinimide type friction modifier (S3) also shows a good Brookfield viscosity.

It is understood that lubricant compositions and/or lubricant additives according to an embodiment of the present disclosure may further exhibit sufficient durability in friction performance.

At numerous places throughout this specification, reference has been made to a number of U.S. Patents, European Patent Applications (published), PCT International patent publications, and literature references. All such cited documents are expressly incorporated in full into this disclosure as if fully set forth herein.

While the present disclosure has been principally demonstrated hereinabove in the examples as a power transmitting fluid having improved low temperature viscometrics for transmissions, it is contemplated that the benefits of the fluid embodiment are similarly applicable to other lubricating or power transmitting fluids. Included within the scope of the present disclosure may be, but not limited to, gear oils, hydraulic fluids, engine oils, heavy duty hydraulic fluids, industrial oils, power steering fluids, pump oils, tractor fluids, and universal tractor fluids. Apparatus embodiments may include, but are not limited to, gears, engines, hydraulic mechanisms, power steering devices, pumps and the like incorporating a lubricating fluid according to the present disclosure.

Other embodiments of the present disclosure will be apparent to those skilled in the art from consideration of the specification and practice of the embodiments disclosed and suggested herein. It is intended that the specification and examples be considered as exemplary only, with a true scope and spirit of the disclosure being indicated by the following claims.

What is claimed is:

1. A reaction product, or a tribologically acceptable salt or solvate thereof, obtained by:
   a. reacting a $C_{10}$-$C_{36}$ vinylidene olefin with maleic acid, anhydride, or ester to provide a hydrocarbon-substituted succinic acid, anhydride or ester; and
   b. aminating the said hydrocarbon-substituted succinic acid, anhydride or ester with an effective amount of a compound containing basic nitrogen,
   wherein said $C_{10}$-$C_{36}$ vinylidene olefin represents the following formula:

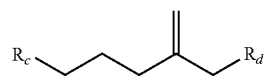

V wherein $R_c$ and $R_d$ are independently a ($C_3$-$C_{15}$) alkyl, cycloalkyl or cycloalkenyl.

2. The reaction product according to claim 1, selected from the group consisting of:
   (5-methylnonadec-5-en-4-yl)pyrrolidine-2,5-dione;
   (6-methylnonadec-6-en-5-yl)pyrrolidine-2,5-dione;
   (7-methylnonadec-7-en-6-yl)pyrrolidine-2,5-dione;
   (8-methylnonadec-8-en-7-yl)pyrrolidine-2,5-dione;
   (9-methylnonadec-9-en-8-yl)pyrrolidine-2,5-dione;
   (10-methylnonadec-10-en-9-yl)pyrrolidine-2,5-dione;
   (9-methylnonadec-8-en-10-yl)pyrrolidine-2,5-dione;
   (8-methylnonadec-7-en-9-yl)pyrrolidine-2,5-dione;
   (7-methylnonadec-6-en-8-yl)pyrrolidine-2,5-dione;
   (6-methylnonadec-5-en-7-yl)pyrrolidine-2,5-dione;
   (5-methylnonadec-4-en-6-yl)pyrrolidine-2,5-dione;
   (4-methylnonadec-3-en-5-yl)pyrrolidine-2,5-dione;
   (3-methylnonadec-2-en-4-yl)pyrrolidine-2,5-dione;
   (2,2'-(ethane-1,2-diylbis(azanediyl))bis(ethane-2,1-diyl)) bis(3-(8-methylnonadec-8-en-7-yl)pyrrolidine-2,5-dione);
   (3-methylhenicos-2-en-4-yl)pyrrolidine-2,5-dione;
   (4-methylhenicos-3-en-5-yl)pyrrolidine-2,5-dione;

(5-methylhenicos-4-en-6-yl)pyrrolidine-2,5-dione;
(6-methylhenicos-5-en-7-yl)pyrrolidine-2,5-dione;
(7-methylhenicos-6-en-8-yl)pyrrolidine-2,5-dione;
(8-methylhenicos-7-en-9-yl)pyrrolidine-2,5-dione;
(9-methylhenicos-8-en-10-yl)pyrrolidine-2,5-dione;
(10-methylhenicos-9-en-11-yl)pyrrolidine-2,5-dione;
(11-methylhenicos-11-en-10-yl)pyrrolidine-2,5-dione;
(10-methylhenicos-10-en-9-yl)pyrrolidine-2,5-dione;
(9-methylhenicos-9-en-8-yl)pyrrolidine-2,5-dione;
(8-methylhenicos-8-en-7-yl)pyrrolidine-2,5-dione;
(7-methylhenicos-7-en-6-yl)pyrrolidine-2,5-dione;
(6-methylhenicos-6-en-5-yl)pyrrolidine-2,5-dione;
(5-methylhenicos-5-en-4-yl)pyrrolidine-2,5-dione;
(2,2'-(ethane-1,2-diylbis(azanediyl))bis(ethane-2,1-diyl))
   bis(3-(5-methylhenicos-5-en-4-yl)pyrrolidine-2,5-dione);
(5-methyltricos-5-en-4-yl)pyrrolidine-2,5-dione;
(6-methyltricos-6-en-5-yl)pyrrolidine-2,5-dione;
(7-methyltricos-7-en-6-yl)pyrrolidine-2,5-dione;
(8-methyltricos-8-en-7-yl)pyrrolidine-2,5-dione;
(9-methyltricos-9-en-8-yl)pyrrolidine-2,5-dione;
(10-methyltricos-10-en-9-yl)pyrrolidine-2,5-dione;
(11-methyltricos-11-en-10-yl)pyrrolidine-2,5-dione;
(12-methyltricos-12-en-11-yl)pyrrolidine-2,5-dione;
(11-methyltricos-10-en-12-yl)pyrrolidine-2,5-dione;
(10-methyltricos-9-en-11-yl)pyrrolidine-2,5-dione;
(9-methyltricos-8-en-10-yl)pyrrolidine-2,5-dione;
(8-methyltricos-7-en-9-yl)pyrrolidine-2,5-dione;
(7-methyltricos-6-en-8-yl)pyrrolidine-2,5-dione;
(6-methyltricos-5-en-7-yl)pyrrolidine-2,5-dione;
(5-methyltricos-4-en-6-yl)pyrrolidine-2,5-dione;
(4-methyltricos-3-en-5-yl)pyrrolidine-2,5-dione;
(3-methyltricos-2-en-4-yl)pyrrolidine-2,5-dione;
(2,2'-(ethane-1,2-diylbis(azanediyl))bis(ethane-2,1-diyl))
   bis(3-(5-methyltricos-5-en-4-yl)pyrrolidine-2,5-dione);
(3-methylpentacos-2-en-4-yl)pyrrolidine-2,5-dione;
(4-methylpentacos-3-en-5-yl)pyrrolidine-2,5-dione;
(5-methylpentacos-4-en-6-yl)pyrrolidine-2,5-dione;
(6-methylpentacos-5-en-7-yl)pyrrolidine-2,5-dione;
(7-methylpentacos-6-en-8-yl)pyrrolidine-2,5-dione;
(8-methylpentacos-7-en-9-yl)pyrrolidine-2,5-dione;
(9-methylpentacos-8-en-10-yl)pyrrolidine-2,5-dione;
(10-methylpentacos-9-en-11-yl)pyrrolidine-2,5-dione;
(11-methylpentacos-10-en-12-yl)pyrrolidine-2,5-dione;
(12-methylpentacos-11-en-13-yl)pyrrolidine-2,5-dione;
(13-methylpentacos-13-en-12-yl)pyrrolidine-2,5-dione;
(12-methylpentacos-12-en-11-yl)pyrrolidine-2,5-dione;
(11-methylpentacos-11-en-10-yl)pyrrolidine-2,5-dione;
(10-methylpentacos-10-en-9-yl)pyrrolidine-2,5-dione;
(9-methylpentacos-9-en-8-yl)pyrrolidine-2,5-dione;
(8-methylpentacos-8-en-7-yl)pyrrolidine-2,5-dione;
(7-methylpentacos-7-en-6-yl)pyrrolidine-2,5-dione;
(6-methylpentacos-6-en-5-yl)pyrrolidine-2,5-dione;
(5-methylpentacos-5-en-4-yl)pyrrolidine-2,5-dione;
(2,2'-(ethane-1,2-diylbis(azanediyl))bis(ethane-2,1-diyl))
   bis(3-(7-methylpentacos-7-en-6-yl)pyrrolidine-2,5-dione); and a tribologically acceptable salt or solvate thereof.

3. A lubricant composition comprising one or more reaction products according to claim 1, or a tribologically acceptable salt or solvate thereof.

4. A lubricant additive composition comprising one or more reaction products according to claim 1, or a tribologically acceptable salt or solvate thereof.

* * * * *